United States Patent
Olsson et al.

(10) Patent No.: US 9,769,366 B2
(45) Date of Patent: Sep. 19, 2017

(54) SELF-GROUNDING TRANSMITTING PORTABLE CAMERA CONTROLLER FOR USE WITH PIPE INSPECTION SYSTEM

(71) Applicants: Mark S. Olsson, La Jolla, CA (US); Dawn E. Shaffer, San Diego, CA (US)

(72) Inventors: Mark S. Olsson, La Jolla, CA (US); Dawn E. Shaffer, San Diego, CA (US)

(73) Assignee: SEESCAN, INC., San Diego, CA (US)

( * ) Notice: Subject to any disclaimer, the term of this patent is extended or adjusted under 35 U.S.C. 154(b) by 454 days.

(21) Appl. No.: 13/941,381

(22) Filed: Jul. 12, 2013

(65) Prior Publication Data
US 2014/0204197 A1    Jul. 24, 2014

Related U.S. Application Data

(60) Provisional application No. 61/671,644, filed on Jul. 13, 2012, provisional application No. 61/784,854, filed on Mar. 14, 2013.

(51) Int. Cl.
| | | |
|---|---|---|
| H04N 5/232 | (2006.01) | |
| G03B 37/00 | (2006.01) | |
| G01N 21/954 | (2006.01) | |
| H04N 5/225 | (2006.01) | |

(52) U.S. Cl.
CPC ....... H04N 5/23203 (2013.01); G03B 37/005 (2013.01); *G01N 2021/9548* (2013.01); *H04N 2005/2255* (2013.01)

(58) Field of Classification Search
CPC ........... H04N 7/185; H04N 2005/2255; H04N 5/23203; G01N 21/954; G01N 2021/9548; G03B 37/005; G02B 23/2492; G02B 23/2476

USPC ....... 348/82, 83, 84, 85, 211.4, 211.7, 211.8, 348/211.14
See application file for complete search history.

(56) References Cited

U.S. PATENT DOCUMENTS

| | | | | |
|---|---|---|---|---|
| 5,194,812 A | * | 3/1993 | Yokoi | G01V 3/06 324/326 |
| 5,264,795 A | * | 11/1993 | Rider | G01V 3/06 324/326 |
| 5,585,726 A | * | 12/1996 | Chau | G01V 3/26 175/45 |

(Continued)

OTHER PUBLICATIONS

International Searching Authority, "Written Opinion of the International Searching Authority" for PCT Patent Application No. PCT/US14/029264, dated Sep. 14, 2015, European Patent Office, Munich.

*Primary Examiner* — John Villecco
(74) *Attorney, Agent, or Firm* — Steven C. Tietsworth, Esq.

(57) ABSTRACT

A portable camera controller for use with a pipe inspection system is disclosed. The controller may include an onboard display, USB ports, wireless capability, and a built-in transmitter for energizing a pipe-inspection cable for tracing purposes. The camera controller may be configured to support auto-logging and automatic report generation of pipe inspection operations and associated locating operations. The camera controller may be self-grounding using conductive and/or capacitive grounding circuits and an associated transmitter may be used without a separate grounding stake through use of the conductive and/or capacitive grounding circuits.

24 Claims, 25 Drawing Sheets

(56) References Cited

U.S. PATENT DOCUMENTS

| | | | | |
|---|---|---|---|---|
| 5,698,981 A * | 12/1997 | Mercer | | G01V 3/26 324/329 |
| 6,079,506 A * | 6/2000 | Mercer | | E21B 7/046 175/45 |
| 6,356,082 B1 * | 3/2002 | Alkire | | G01V 3/06 324/326 |
| 6,411,094 B1 * | 6/2002 | Gard | | E21B 44/00 175/45 |
| 6,427,784 B1 * | 8/2002 | Archambeault | | E21B 47/024 175/45 |
| 6,776,246 B1 * | 8/2004 | Nickel | | E21B 7/046 175/40 |
| 7,336,078 B1 * | 2/2008 | Merewether | | G01V 3/15 324/326 |
| 7,460,980 B2 | 12/2008 | Hinn | | |
| 7,466,135 B2 * | 12/2008 | Mercer | | E21B 47/02224 324/329 |
| 8,264,226 B1 * | 9/2012 | Olsson | | G01V 3/15 324/326 |
| 8,289,385 B2 * | 10/2012 | Olsson | | H01B 7/182 174/107 |
| 8,395,661 B1 | 3/2013 | Olsson et al. | | |
| 8,547,428 B1 * | 10/2013 | Olsson | | G03B 37/005 348/374 |
| 9,057,471 B2 * | 6/2015 | Kokoski | | F16L 41/04 |
| 9,222,809 B1 * | 12/2015 | Olsson | | B65H 75/00 |
| 2002/0113870 A1 | 8/2002 | Mueckl et al. | | |
| 2002/0166396 A1 * | 11/2002 | McGrew | | G01M 3/38 73/865.8 |
| 2005/0105261 A1 * | 5/2005 | Bhogal | | G06F 1/183 361/679.55 |
| 2005/0129108 A1 * | 6/2005 | Bendall | | A61B 1/00039 375/240.01 |
| 2007/0297778 A1 * | 12/2007 | Lange | | G03B 37/005 396/19 |
| 2009/0225159 A1 * | 9/2009 | Schneider | | A61B 1/00124 348/82 |
| 2010/0001712 A1 * | 1/2010 | Royle | | G01V 3/15 324/67 |
| 2010/0208055 A1 * | 8/2010 | Olsson | | H01B 7/182 348/84 |
| 2010/0208056 A1 * | 8/2010 | Olsson | | H04N 7/185 348/84 |
| 2011/0108654 A1 * | 5/2011 | Babb | | B65H 75/364 242/400 |
| 2011/0109437 A1 * | 5/2011 | Olsson | | G01V 3/15 340/8.1 |
| 2011/0186203 A1 * | 8/2011 | Lindner | | B32B 37/02 156/64 |
| 2011/0196534 A1 * | 8/2011 | Ekes | | F16L 55/48 700/259 |
| 2012/0147173 A1 * | 6/2012 | Lynch | | G03B 37/005 348/84 |
| 2012/0300057 A1 * | 11/2012 | Bartucciotto | | F16L 55/48 348/84 |
| 2012/0306603 A1 | 12/2012 | Olsson | | |
| 2013/0329086 A1 * | 12/2013 | Malone | | G06F 17/30038 348/231.99 |
| 2014/0147086 A1 * | 5/2014 | Chapman | | H01B 11/22 385/101 |
| 2014/0167766 A1 * | 6/2014 | Olsson | | G01V 3/165 324/329 |
| 2014/0210989 A1 * | 7/2014 | Olsson | | H04N 5/232 348/84 |
| 2014/0320133 A1 * | 10/2014 | Olsson | | G01V 3/10 324/329 |
| 2014/0340505 A1 * | 11/2014 | Olsson | | G01N 21/8803 348/84 |

\* cited by examiner

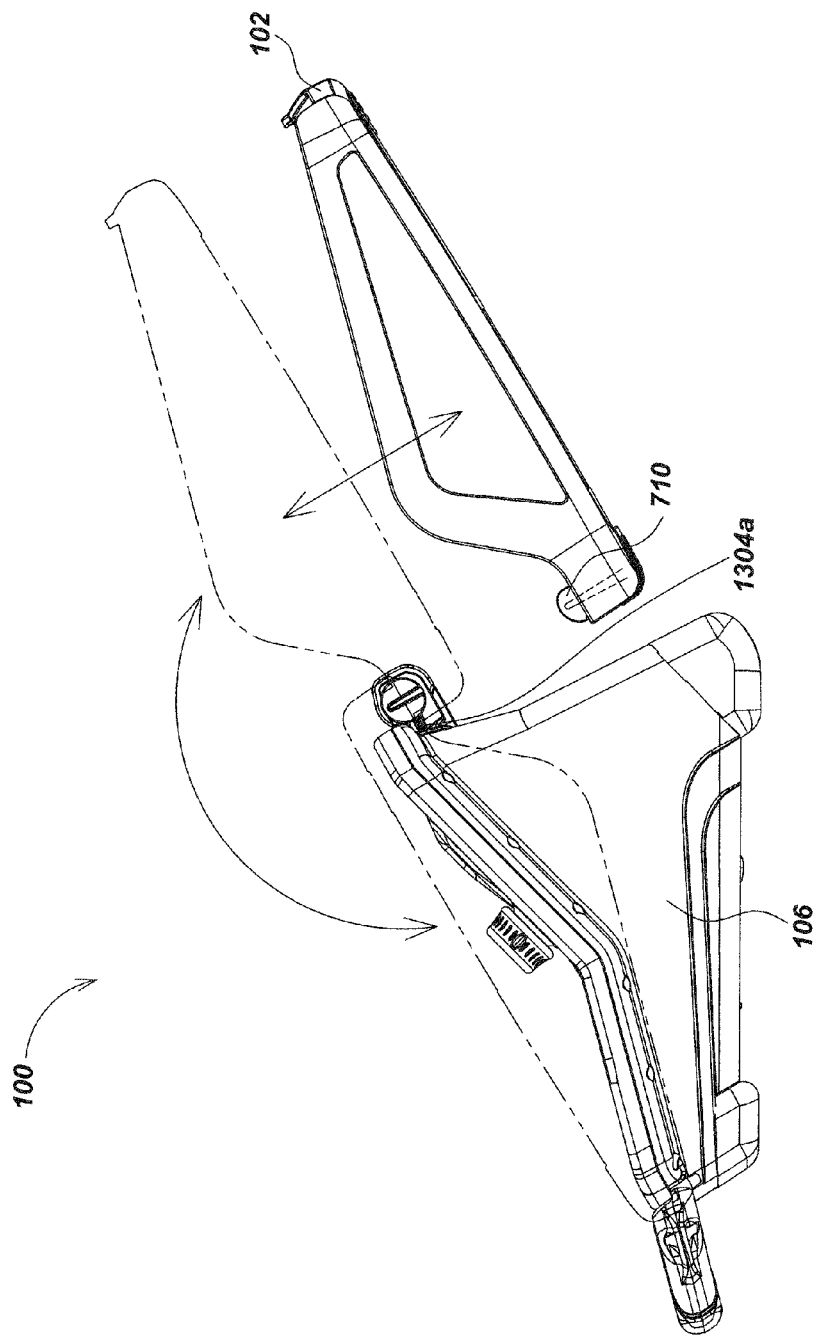

SELF-GROUNDING TRANSMITTING PORTABLE CAMERA CONTROLLER FOR USE WITH PIPE INSPECTION SYSTEM

CROSS-REFERENCE TO RELATED APPLICATIONS

This applications claims priority under 35 U.S.C. § 119(e) to U.S. Provisional Patent Application Ser. No. 61/671,644, entitled SELF-GROUNDING TRANSMITTER POR-TABLE CAMERA CONTROLLER FOR USE WITH PIPE INSPECTION SYSTEM, filed Jul. 13, 2012 and to U.S. Provisional Patent Application Ser. No. 61/784,854, entitled SELF-GROUNDING TRANSMITTING PORTABLE CAMERA CONTROLLER FOR USE WITH PIPE INSPECTION SYSTEM, filed Mar. 14, 2013. The content of each of these applications is hereby incorporated by reference herein in its entirety for all purposes.

FIELD

This disclosure relates generally to portable pipe inspection systems and related accessories and apparatus. More specifically, but not exclusively, the disclosure relates to camera controllers for use with pipe inspection systems.

BACKGROUND

Pipes are often prone to obstructions through a variety of mechanical, structural, and/or environmental factors, such as for example, invasion by tree roots and/or other vegetation, build-up and corrosion, as well as other blockages. Various devices and methods for visualizing the interior of a pipe are known in the art. For example, current pipe inspection systems typically include a camera head coupled to the end of a cable to inspect the interior of pipes, conduits, and other voids, and the images collected are elucidated on a display device. However, current systems are often bulky and difficult to transport to a remote location. Traditional pipe-inspection camera controllers have minimum intelligence built in aside from directly controlling the inspection camera, and do not synchronize or exchange information with other devices generally.

SUMMARY

The present disclosure relates generally to apparatus, systems, and methods for pipe inspection. More specifically, but not exclusively, the disclosure relates to a portable camera controller and associated pipe inspection system.

For example, in one aspect, the disclosure relates to a portable camera controller system such as for use in inspection of a pipe as part of a pipe inspection system. A pipe inspection system may include, for example, a camera head coupled to the end of a push-cable, a cable storage drum, and a camera controller, which may include a base assembly or base structure configured for ease of portability. The camera controller may further include, for example, an electronic computing device, such as a computer or display device, which may be mounted to the base. The camera controller may include, for example, a user interface device or element to provide data exchange between the camera head and display device. The interface may include, for example, a front panel configured with a control keypad, touch screen, or other user interface element. The camera controller may include a user input device such as a magnetic user interface device which may control camera view, as a joystick control, or act as a user control mouse device, for example. In another aspect, such a device may act as a data controller such as a software input device, or may be configured to control mechanical components in a remote camera device such as carrier wheels, remote switches or valves, or connected electromechanical, hydraulic or pneumatic devices, for example.

In another aspect, a camera controller system may include, for example, a built-in transmitter which may be used to transmit one or more frequencies of electromagnetic signal along a pipe inspection push-cable when in use. In another aspect, such a transmitter may internally connect to the push-cable within the body of the camera controller, for example. In another aspect of the present disclosure, the camera controller may be constructed using conductive materials in supporting members which contact the ground when deployed, allowing the camera controller to be self-grounding without the use of an external ground stake, for example. In another aspect, such grounding may be achieved by capacitative coupling, by conductive coupling, or by a combination of both, for example. In another aspect, conductive paint and/or plating applied internally to the inner structure or interior casing of a camera controller body may act as an element of a grounding circuit. Alternatively metal sheeting, metal posts or other conductive elements may be used in the interior structure and grounded to act as a part of the grounding circuit for an internal transmitter.

The camera controller system may further include, for example, a processing element including a processor and a USB bus connected to the processor. The camera controller may further include, for example, a system cable plug or connector for connecting the camera controller to an interface circuit coupled to the cable storage drum, a push-cable and a camera head. The camera controller system may further include, for example, a control pad on a user interface for providing control commands to the camera head. Programming may be stored at least partially in firmware in the camera controller, enabling the control pad to interact with the pipe inspection system.

In another aspect, the disclosure relates to a portable camera controller which may be configured to be fully or partially integrated with a pipe inspection system by direct electrical connection. The electronics module may include one or more processing elements configured to receive control input signals from the user interface panel and provide control data to the pipe inspection system. The processing element(s) may be further configured to receive one or more pipe inspection output signals from the pipe inspection system and provide data corresponding to the pipe inspection output signals to an electronic computing system.

In another aspect, the disclosure relates to a camera controller configured with wireless modules to implement wireless communication capabilities including, for example, Bluetooth, ISM radio, wireless local area network (WLAN), and GPS reception by means of which images, information and control data relating to a pipe-inspection and locating operation may be shared among associated devices.

In another aspect, the disclosure relates to a camera controller equipped with orientation and movement sensors such as gyroscopic sensors, accelerometers, solid-state compass devices or GPS receivers to provide continuous location information during an inspection and locating operation. A camera assembly may be equipped with a transmitting beacon which may be used by a locating receiver to compute the precise distance and orientation between, for example, the beacon and the locating receiver for use in reporting and mapping applications related to the pipe inspection and locating operation.

In some embodiments, a pipe inspection camera may be equipped with integrated circuit sensors including, for example, gyroscopic sensors, accelerometers, a microphone and/or solid-state compass devices combined with a high-speed data link to a camera controller, allowing the controller to map the path of the camera through a piping system. An operator using such a system would be able to monitor the sounds at the camera head to aid in diagnosis of situations in the pipe.

In another aspect, the disclosure relates to a camera controller which may include, for example, a plurality of electronic ports configured to accept USB devices and connect them to an internal USB bus. The controller may be configured to use such devices, for example, to store images received from the associated inspection camera serially or as video segments, for example, or to store audio captured during the process of a pipe inspection such as operator commentary, for example.

In another aspect, the disclosure relates to methods and processing for implementing the camera controller system functionality as described above, in whole or in part.

In another aspect, the disclosure relates to means for implementing the above-described methods and/or system or device functions, in whole or in part.

In another aspect, the disclosure relates to computer-readable media including instructions for causing a computer or processing element to implement the camera system functionality described above, in whole or in part.

Various additional aspects, features, and functionality are further described below in conjunction with the appended Drawings.

BRIEF DESCRIPTION OF THE DRAWINGS

The present disclosure may be more fully appreciated in connection with the following detailed description taken in conjunction with the accompanying drawings, wherein:

FIG. 15B is an illustration of the protective cover being removed;

DETAILED DESCRIPTION

Figure 1A:
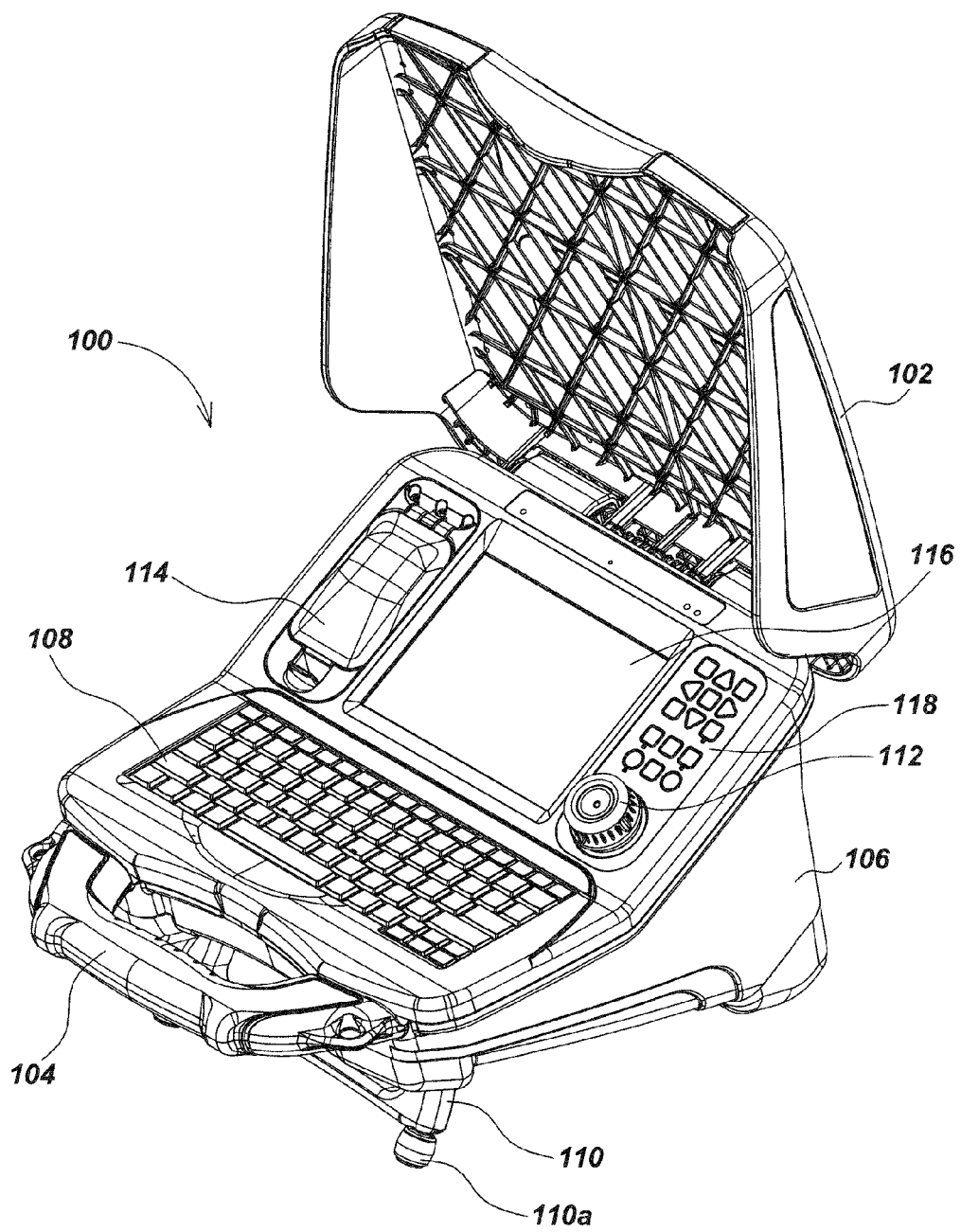
FIG. 1A is an isometric view of an embodiment of a portable camera controller.

Various aspects of pipe inspection components, accessories, methods, configurations, and systems that may be used in conjunction with the disclosure herein in various embodiments are described in U.S. Patent Application Ser. No. 61/607,510, entitled DUAL SENSED LOCATING SYSTEMS & METHODS, filed Mar. 6, 2012, U.S. Patent Application Ser. No. 61/430,932, entitled PORTABLE CAMERA CONTROLLER PLATFORM FOR USE WITH PIPE INSPECTION SYSTEM, filed on Jan. 7, 2011, U.S. Patent Application Ser. No. 61/602,065, entitled DOCKABLE TRIPODAL CAMERA CONTROL UNIT, filed on Feb. 22, 2012, U.S. Patent Application 61/618,746, filed on Mar. 31, 2012, entitled DUAL ANTENNA SYSTEMS WITH VARIABLE POLARIZATION, and U.S. Provisional Patent Application Ser. No. 61/152,662, entitled HIGH PERFORMANCE PIPE INSPECTION SYSTEM, filed Feb. 13, 2009. The content of each of these applications is incorporated by reference herein in its entirety.

Various aspects of manual user interface device apparatus, devices, configurations, methods, and systems that may be used in conjunction with the controller embodiments of the disclosure herein are described in U.S. Utility patent application Ser. No. 13/310,670, filed Dec. 2, 2011, entitled MAGNETICALLY SENSED USER INTERFACE APPARATUS AND DEVICES, U.S. Utility patent application Ser. No. 13/292,038, filed Nov. 8, 2011, entitled SLIM PROFILE MAGNETIC USER INTERFACE DEVICES, U.S. Utility patent application Ser. No. 13/272,172, filed Oct. 12, 2011, entitled MAGNETIC THUMBSTICK USER INTERFACE DEVICES, U.S. Utility patent application Ser. No. 13/214,209, filed Aug. 21, 2011, entitled MAGNETIC SENSING USER INTERFACE DEVICE METHODS AND APPARATUS, U.S. Utility patent application Ser. No. 13/774,351, entitled DOCKABLE TRIPODAL CAMERA CONTROL UNIT, filed Feb. 22, 2013, U.S. Utility patent application Ser. No. 12/939,591, entitled SMART PERSONAL COMMUNICATION DEVICES AS USER INTERFACES, filed Nov. 4, 2010, and U.S. Utility patent application Ser. No. 13/110,910, filed May 18, 2011, entitled USER INTERFACE DEVICES, APPARATUS, & METHODS. The content of each of these applications is incorporated by reference herein in its entirety.

Terminology

The term "electronic computing device" as used herein refers to an electronic device or system including data input, processing, and display functionality and optionally other functionality such as receiving user input and control actions, providing data storage, communications interfaces to external devices or systems, as well as providing other computer-related functions. Examples of electronic computing devices include, but are not limited to, personal computer devices such as laptop or notebook computers, tablet devices, such as Android or iPad devices, smart phones, and similar devices. In some embodiments, electronic computing devices may also include other devices such as monitoring and control system devices, instrumentation devices, or other similar or equivalent computer or processor-based systems or devices that include processing and display functionality.

The terms "processing element" or "processing module" as used herein refer to an electronic circuit for performing signal and data processing functions, control functions, and other digital processing functions as described herein. A processing element may be implemented or processing functions performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, special purpose processing and/or state machine or other programmable device. A processor may also be implemented as a combination of computing devices, e.g., a combination of a DSP and a microprocessor, a plurality of microprocessors, one or more microprocessors in conjunction with a DSP core, or any other such configuration. A processing element may furthering include or be coupled to one or more memory elements, for storing instructions, data, and/or other information in a digital storage format, as well as interface and signal conditioning element, Input/Output (I/O) elements and the like.

The term "interface bus" as used herein refers to a communications interface circuit and related components for digitally interfacing different electronic devices. Examples of interface buses include, but are not limited to, Universal Serial Bus (USB) interfaces, Firewire™ interfaces, other serial or parallel interfaces, as well as other computer or digital data interfaces known or developed in the art.

The term "electronics module" as used herein relates to a module including electronic components for providing the control and signal processing and related functions as described herein in conjunction with pipe inspection systems and devices. An electronics module may include analog circuits, digital circuits, mechanical and electronic hardware, firmware stored in a programmable memory or device, and/or software components stored on a non-transitory medium, which may be mounted or disposed on or in one or more printed circuit boards or other circuit elements and related mechanical assemblies. An electronics module may use one or more processing elements to perform signal processing and related functions, and may further include analog signal conditioning circuits, as well as analog or digital circuits to receive and send data or information within a camera controller and/or externally to or from the camera controller. Additional components, such as keypads, displays, switches, sensors, memory devices, input/output devices, wired, radio, and/or optical interface modules, sensors, position determination modules, such as GPS or other location-identification modules, inertial location devices, or other elements such as are described herein may be included in or coupled to electronics modules in various implementations.

The word "exemplary" is used herein to mean "serving as an example, instance, or illustration." Any aspect and/or embodiment described herein as "exemplary" is not necessarily to be construed as preferred or advantageous over other aspects and/or embodiments.

Overview

This disclosure relates generally to pipe inspection systems and related accessories and apparatus. More specifically, but not exclusively, the disclosure relates to portable camera controllers for use with a pipe inspection system as well as accessories and methods of use.

For example, in one aspect, the disclosure relates to a portable camera controller system such as for use in inspection of a pipe as part of a pipe inspection system. A pipe inspection system may include, for example, a camera head coupled to the end of a push-cable, a cable storage drum, and a camera controller, which may include a base assembly or base structure configured for ease of portability. The camera controller may further include, for example, an electronic computing device, such as a computer or display device, which may be mounted to the base. The camera controller may include, for example, a user interface device or element to provide data exchange between the camera head and display device. The interface may include, for example, a front panel configured with a control keypad, touch screen, or other user interface element. The camera controller may include a user input device such as a magnetic user interface device which may control camera view, as a joystick control, or act as a user control mouse device, for example. In another aspect, such a device may act as a data controller such as a software input device, or may be configured to control mechanical components in a remote camera device such as carrier wheels, remote switches or valves, or connected electromechanical, hydraulic or pneumatic devices, for example.

In another aspect, a camera controller system may include, for example, a built-in transmitter which may be used to transmit one or more frequencies of electromagnetic signal along a pipe inspection push-cable when in use.

In another aspect, a camera controller may include a display device, and an electronic computing device for enabling such a display device to be conveniently used as a pipe-inspection system monitor and a virtual control interface. The camera controller may additionally include an input device, such as a control keyboard or other input device, and may optionally include a built-in user interface device, such as, for example, a mouse joystick, or magnetic user interface device, such as is described in the incorporated applications, which may serve as a mouse or a joystick and/or provide additional user interface functionality such as providing switching inputs, twist-type inputs, push-pull inputs, etc. A plurality of virtual controls may be supported by a software application installed on, or accessed by, the computing device connected to the camera controller or built in to it. In an alternative embodiment the camera controller may be wirelessly controlled by a remote device such as a smart phone or a handheld tablet. The camera controller may contain a plurality of electromechanical ports suitable for connecting portable memory devices such as, for example, USB thumb drives or the like for the storage, transport or relay of pipe-inspection images, video clips, audio commentary, positional or locational information, and the like.

In another aspect, a portable camera controller provides an electrical connection mechanism suitable for connection to a pipe-inspection push-cable with a pipe-inspection camera mounted on it. The camera controller may include, for example, circuitry for exchanging data, files, and control commands with a camera head coupled to the end of a push-cable. The camera controller may, in another aspect, be configured with control input devices such as, for example, a multi-directional mouse or joystick, suitable for issuing controls to a camera, or to camera transport elements, or camera motion-control elements associated with the camera head, for example. The camera controller may include a base assembly or base structure configured for connecting to a cable storage drum or connecting to the pipe-inspection cable stored on such a drum, for example, by wired connection or by wireless means. The camera controller system may include, for example, a system cable plug or connector for connecting the controller to an interface circuit coupled to the cable storage drum and a camera head, using a system connector cable.

The camera controller may further include, for example, a user interface device or element to provide data and control exchange between the camera head and display device. The interface may include, for example, a front panel configured with a control keypad, touch screen, or other user interface element, such as a magnetic user interface device, joystick, mouse, touchpad, or the like. The camera controller may include a wireless link to a portable touchpad, smart phone, or digital assistant used as an interface device.

In another aspect, the camera controller system may further include, for example, a processing element including a processor and a USB bus electrically coupled to the processor. The camera controller system may further include, for example, a system cable plug or connector for connecting the controller to an interface circuit coupled to the cable storage drum and a camera head, using a system connector cable. The camera controller system may further include, for example, a control pad on a user interface for providing control commands to the camera head. Programming may be stored at least partially in firmware in the controller, enabling the controller to interact with the pipe inspection system or other devices.

In another aspect, the camera controller system may further include, for example, a memory device, such as a USB device or dongle, flash drive, or other memory storage device.

In another aspect, the disclosure relates to a man-portable camera controller including a Universal Serial Bus (USB) hub coupled to the electronics module. The USB hub may provide a plurality of USB-compatible ports. In one aspect the ports may be disposed at varied depths below the controller exterior for the purpose of allowing higher-capacity USB devices of larger external dimensions to be seated in the deeper ports for longer-terms storage of data.

The camera controller may further include a wireless communication module, for example, coupled to the electronics module for receiving wirelessly communicated signals from a pipe inspection system and/or for sending wireless communication signals to the pipe inspection system, such as to an interface module or other devices such as a portable locator receiver, locational beacon, or separate transmitter, for example. The hub or router may be further configured to provide wired information to or from the pipe inspection system. The information provided from the hub or router may include images or video signals. The information may also include audio or video signals or data, for example. The information may also include location, position, or orientation data or information for example. The information may also include control or feedback data or information. The information may also include sensor or actuator data or information.

The camera output signals received by the camera controller may, for example, be video signals. The video signals may be converted to digital signals in accordance with an interface bus standard. The video signals may be compressed. The interface bus may be a Universal Serial Bus (USB).

The camera controller may further include, for example, a microphone. The electronics module may be further configured to receive an audio signal from the microphone and associate the audio signal with the digital signals, such as with video or images. The output signals from the pipe inspection system may be video signals, and the video signals may be compressed before being provided to the electronic computing system.

In another aspect, the disclosure relates to a camera controller. The camera controller may include a base assembly configured to mechanically couple the camera controller to a pipe inspection system including a cable reel drum assembly and a camera head, a user interface panel disposed on or in the base assembly, and an electronics module coupled to the user interface panel. The electronics module may include one or more processing elements configured to receive control input signals from the user interface panel and provide control data to the pipe inspection system, and receive one or more pipe inspection output signals from the pipe inspection system and provide data corresponding to the pipe inspection output signals to an electronic computing system. The system may further include a system connector coupled to the electronics module and to a second end of the system cable. The camera controller may incorporate a hard drive configured to receive and store data including camera image data, voice recording data, GPS data, and time-signal data, for example, for use in recording, storing and correlating the results of a pipe inspection process.

In another aspect, the disclosure relates to a camera controller which may include, for example, a base assembly, a user interface panel disposed on or in the base assembly, and an electronics module coupled to the user interface panel. The electronics module may include one or more processing elements. The processing elements may be configured to receive control input signals from the user interface panel and provide control data to a pipe inspection system, and receive one or more pipe inspection output signals from the pipe inspection system and provide data corresponding to the pipe inspection output signals to an electronic computing system. The camera controller may include a wireless link such as Bluetooth, wireless local area network, and/or an ISM radio link, for example, by means of which image data, location data, transmission frequency data, and other data may be transmitted to an associated locator receiver for synchronization and display. For example, images from the camera during a pipe inspection may be transmitted to a locator being used to trace the inspection cable, at a certain rate such as 1 frame per second, providing the operator with a view from the camera coordinated with the trace information. The camera controller assembly may include one or more primary battery connectors or ports to contain user-replaceable batteries such as rechargeable lithium-ion batteries, for example. The camera controller assembly may likewise include one or more auxiliary on-board battery ports supporting an auxiliary battery to provide data retention when other sources of power are not present, for example.

In another aspect, the disclosure relates to a camera controller configured for use with a pipe mapping system such as described in, for example, U.S. patent application Ser. No. 11/928,818, filed Oct. 30, 2007, entitled PIPE MAPPING SYSTEM, the contents of which are incorporated by reference herein.

The camera controller may include communication radio module such as an ISM radio, Bluetooth, or modules for providing other wireless data communication links, for example, and may use such links to exchange information wirelessly with a locator, a remote beacon or beacon receiver, a separate transmitter, or other associated devices in a locating or pipe inspection operation. For example, images from the camera received by the camera controller may be transmitted to a locator for local display to a locator operator who is tracing the push-cable. For another example, the camera controller may receive GPS locational data from a locator and may receive data concerning detected depth and location of a target conductor such as a push-cable, for example. The camera controller may include processors capable of processing such data and correlating it with images, for example, from the camera head for the correlated location. The camera controller may include, for example, a beacon transmitter signals from which may be detected and correlated by a locator receiver to determine the relative location and distance of the locator receiver from the camera controller, and such information may be transmitted back to the camera controller from the locating receiver and integrated into data collected by, correlated by and stored onboard the camera controller processor elements and storage devices, for example.

In another aspect, the disclosure relates to methods and processing for implementing the camera controller functionality as described above, in whole or in part.

In another aspect, the disclosure relates to means for implementing the above-described methods and/or system or device functions, in whole or in part.

In another aspect, the disclosure relates to computer-readable media including instructions for causing a computer or processing element to implement the camera controller functionality described above, in whole or in part.

Various additional aspects, features, and functionality are further described below in conjunction with the appended Drawings.

Various aspects of antenna configurations and beacon antenna configurations that may be used in conjunction with the camera controller embodiments and locator receiver devices described in the present disclosure are described in U.S. Patent Application 61/618,746, filed on Mar. 31, 2012, entitled DUAL ANTENNA SYSTEMS WITH VARIABLE POLARIZATION. The content of this application is hereby incorporated by reference herein in its entirety for all purposes.

Various aspects and details of pipe inspection system devices, configurations, and methods which may be used in embodiments of the present invention in conjunction with the disclosure herein are described in co-assigned patent applications, including, for example, U.S. Patent Application Ser. No. 61/607,510, entitled DUAL SENSED LOCATING SYSTEMS & METHODS, filed Mar. 6, 2012, U.S. Patent Application Ser. No. 61/430,932, entitled PORTABLE CAMERA CONTROLLER PLATFORM FOR USE WITH PIPE INSPECTION SYSTEM, filed on Jan. 7, 2011, U.S. Patent Application Ser. No. 61/602,065, entitled DOCKABLE TRIPODAL CAMERA CONTROL UNIT, filed on Feb. 22, 2012, U.S. patent application Ser. No. 13/774,351, entitled DOCKABLE TRIPODAL CAMERA CONTROL UNIT, filed Feb. 22, 2013, and U.S. Provisional Patent Application Ser. No. 61/152,662, entitled HIGH PERFORMANCE PIPE INSPECTION SYSTEM, filed Feb. 13, 2009. The content of each of these applications is hereby incorporated by reference herein in its entirety for all purposes.

Various aspects of manual user interface device apparatus, devices, configurations, and methods that may be used in conjunction with the controller embodiments of the disclosure herein are described in U.S. Utility patent application Ser. No. 13/310,670, filed Dec. 2, 2011, entitled MAGNETICALLY SENSED USER INTERFACE APPARATUS AND DEVICES, U.S. Utility patent application Ser. No. 13/292,038, filed Nov. 8, 2011, entitled SLIM PROFILE MAGNETIC USER INTERFACE DEVICES, U.S. Utility patent application Ser. No. 13/272,172, filed Oct. 12, 2011, entitled MAGNETIC THUMBSTICK USER INTERFACE DEVICES, U.S. Utility patent application Ser. No. 13/214,209, filed Aug. 21, 2011, entitled MAGNETIC SENSING USER INTERFACE DEVICE METHODS AND APPARATUS, and U.S. Utility patent application Ser. No. 13/110,910, filed May 18, 2011, entitled USER INTERFACE DEVICES, APPARATUS, & METHODS. The content of each of these applications is hereby incorporated by reference herein in its entirety for all purposes.

The following exemplary embodiments are provided for the purpose of illustrating examples of various aspects, details, and functions of apparatus, methods, and systems for inspecting the interior of pipes, conduits, and other voids; however, the described embodiments are not intended to be in any way limiting. It will be apparent to one of ordinary skill in the art that various aspects may be implemented in other embodiments within the spirit and scope of the present disclosure.

Example Embodiments

Referring to FIG. 1A, a camera controller embodiment 100 in accordance with aspects of the present disclosure is illustrated. Camera controller 100 may include a base assembly for providing mechanical coupling to additional pipe inspection system elements such as a cable reel assembly and camera head and/or other elements such as are described herein. Camera controller 100 may include a shading element, such as protective cover 102, which may be configured to serve as a sunshade to reduce glare when the controller is deployed in an open configuration, such as shown in FIG. 1A. The camera controller 100 may further be fitted with a carrying handle 104. The camera controller 100 may include a formed outer case 106 to which the protective cover 102 may be attached. The camera controller 100 may include one or more user input devices such as a keyboard 108, touchpad, computer mouse, or other user input devices such as those described in the incorporated applications. The keyboard 108 may be protected from liquids or other contaminants by a cover element, such as by a molded skin secured by a light-tack adhesive, for example.

In conjunction with the case 106, the camera controller 100 may include a support structure, such as deployable kickstand 110, which may attach to the outer case 106 and support it, such as on the ground or on other surfaces, when deployed. The support structure or base structure, such as kickstand 110 and the feet 110a, may be formed of conductive material to provide an electrical grounding connection when deployed on ground surfaces such as soil, grass, or other electrically conductive surfaces. The mounting of the kickstand 110, and/or other case or attached elements (not shown), may also be conductive to assist in forming a ground path when an internal transmitter (not shown) of controller 100 is used. The kickstand 110 may be configured to flex in order to release the hinge from detents and to snap into detents formed in the hinge socket, for example. In an alternative embodiment, the kickstand may be fitted with springs or other pressure-applying elements, such as, for example, a doubled layer of 0.020 17-4 APH spring steel, such that it may be retained against the case 106 when not deployed and retained in the open position when deployed.

Figure 1B:
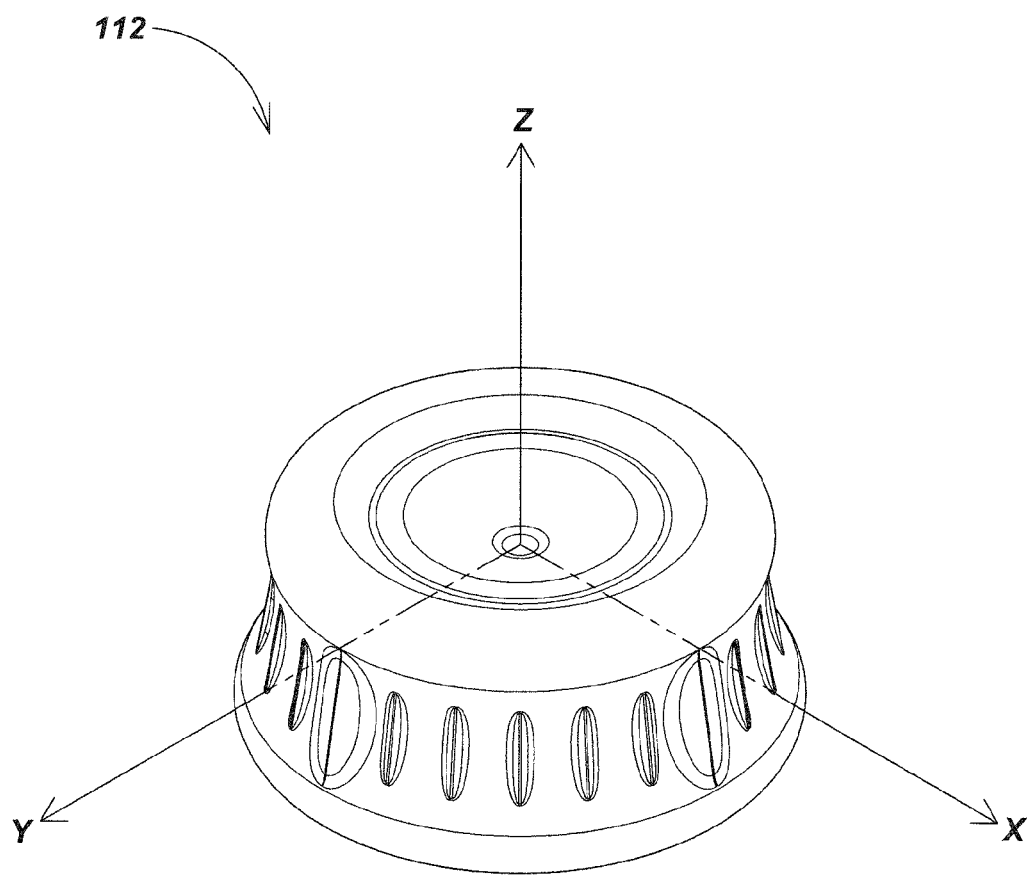
FIG. 1B is a detailed view of a magnetic mouse and joystick.

The camera controller 100 may be fitted with one or more user interface device such as a magnetic mouse and joystick 112 as illustrated in greater detail in FIG. 1B, for example, or a trackball or similar user interface device. The user interface device may be a magnetically sensed user input device as described in the incorporated applications. The user interface devices may be used for controlling display elements, selecting display items, inputting controls for camera angles and motion or the like, or for providing other control functionality. The magnetic mouse and joystick 112 may be configured to control devices associated with a camera such as a camera transporter, end effectors, valves or other associated optical, electromechanical or mechanical devices. A sewer tractor or crawler may be configured, for instance, to move forward, backward and/or turn by the magnetic mouse and joystick 112. The magnetic mouse and joystick 112 may also be enabled to move a mouse cursor on screen. The magnetic mouse and joystick 112 may also be used to pan, zoom, and rotate image views or camera angles, for example. Optionally, a touch pad, touch screen, or a linked tablet device, smart phone, notebook computer, or other computing device with touch screen capabilities may be used for user input. User input devices may be linked wirelessly to the controller 100 and/or may have wired connections such as, for example, through a USB port, Ethernet port, and the like.

Returning to FIG. 1A, the camera controller 100 may be fitted with electrical signal connectors, which may be recessed connector ports such as, for example, USB or other device interface ports, and which may be shielded from water and dust by a port cover 114. Images received from the camera, informational overlays such as distance counts, for example, operating menus and other information, may be electronically routed to a display screen 116 which may act as a user interface panel or element for receiving inputs from a user related to inspection operations such as cable reel deployment, camera orientation and control, pipe obstruction removal, display control, data or information storage, retrieval, or transmission, or other related functions. The camera controller may include a command panel or keypad 118 configured to transmit control data to the electronic components of the camera controller 100 to manage the camera, camera lights, embedded sonde or camera view capture software, for example, or other commands.

In addition, camera controller 100 may include one or more electronics modules for receiving inputs from users or other components such as the camera head, microphones, positional, location, and/or other sensors, radio and GPS data signals, or other input elements, providing input signal processing, interfacing between components, providing control, data and information storage, and/or other electronic, processing, storage, or data and information transmission functions such as are described herein. For example, images and video data or information, such as compressed digital video or other data or information, may be stored in the electronics module and/or in the electronic computing device or other device or system. Other information or data, such as control data or information, audio data or information, sensor data or information, environmental data or information, location data or information (e.g., position coordinates, such as may be obtained from inertial sensors, GPS modules, etc. that may be included in the camera control or other component of a pipe inspection system), or other data or information. The electronics modules may include one or more processing elements as well as associated components such as analog or digital circuit, input/output circuits, power supply circuits, video and audio circuits, sensor circuits, GPS or other location determination devices, inertial navigation devices, as well as other electronic circuits such as those described subsequently herein. Camera controller 100 may be configured to be coupled to pipe inspection apparatus and systems such as are described in the Pipe Inspection System Applications, incorporated by reference herein.

Figure 2A:
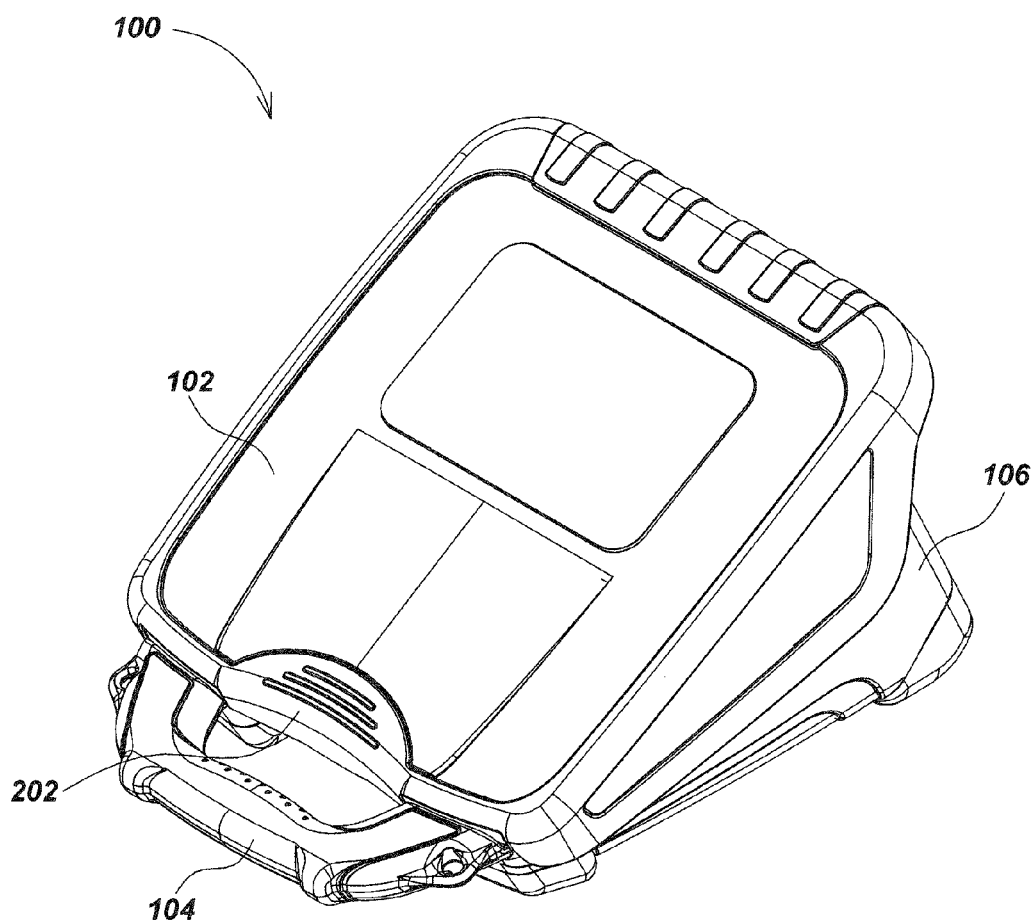
FIG. 2A is a perspective view of the camera controller embodiment of FIG. 1A in its covered configuration.

Turning to FIG. 2A, an exemplary embodiment of a camera controller 100 in a closed or storage configuration is shown. Controller 100 may include a protective cover 102, a carrying handle 104, and an outer case 106, such as shown in FIG. 1A. The molded form of the protective cover 102 may include a formed snap latch 202 to secure the protective cover 102 to the case 106 in a closed configuration for transport.

Figure 2B:
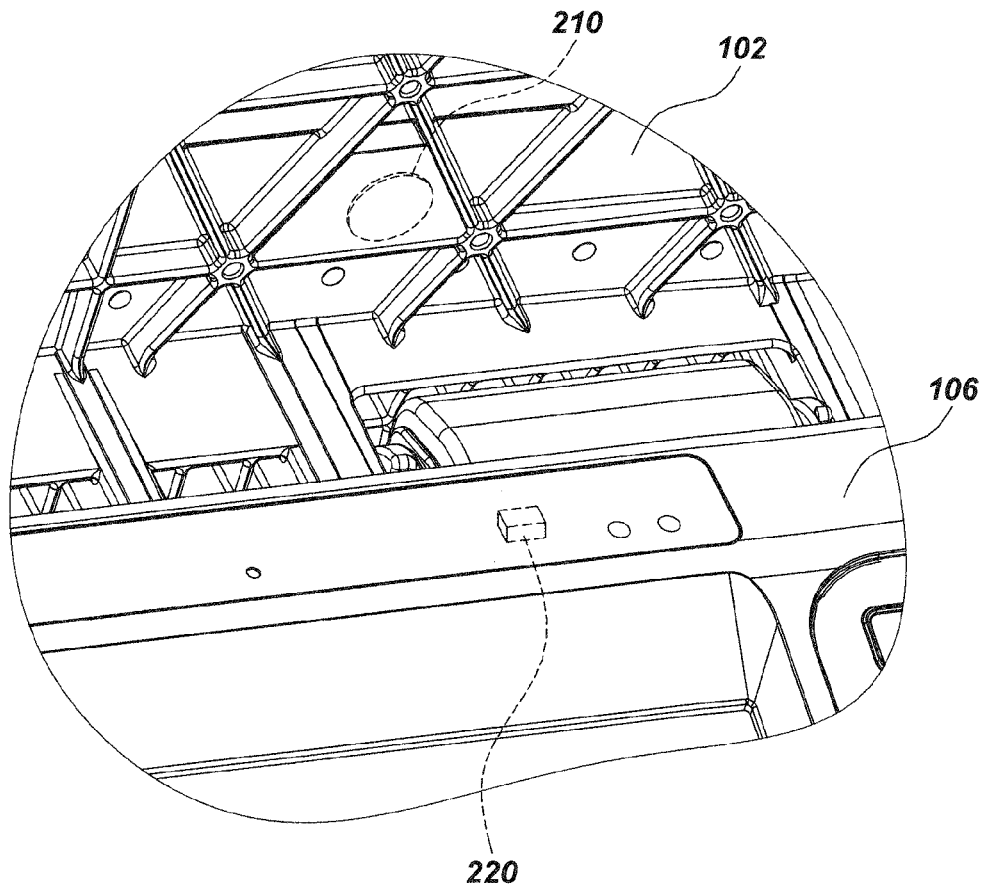
FIG. 2B is a detailed view demonstrating the magnetic and magnetic switch.

Turning to FIG. 2B, a magnet 210 may be secured to or into the protective cover 102 and magnetic switch 220 may be secured onto or within the outer case 106. The magnet 210 and the magnetic switch 220 may be located such that when the protective cover 102 is shut, the magnetic switch 220 may sense the magnet 210 and generate a signal accordingly. In some embodiments, such signal may indicate to the device to enter a stand-by mode or shut down. Furthermore, opening of the protective cover 102 may move the magnet 210 away from the magnetic switch 220 generating signal which may indicate to the device to enter a ready or powered-on state. The magnetic switch 220 may, for instance, be a hall-effect sensor. In alternative embodiments, a magnet may be secured onto or within the outer case 106 and a magnetic switch may be secured to or into the protective cover 102.

Figure 3:
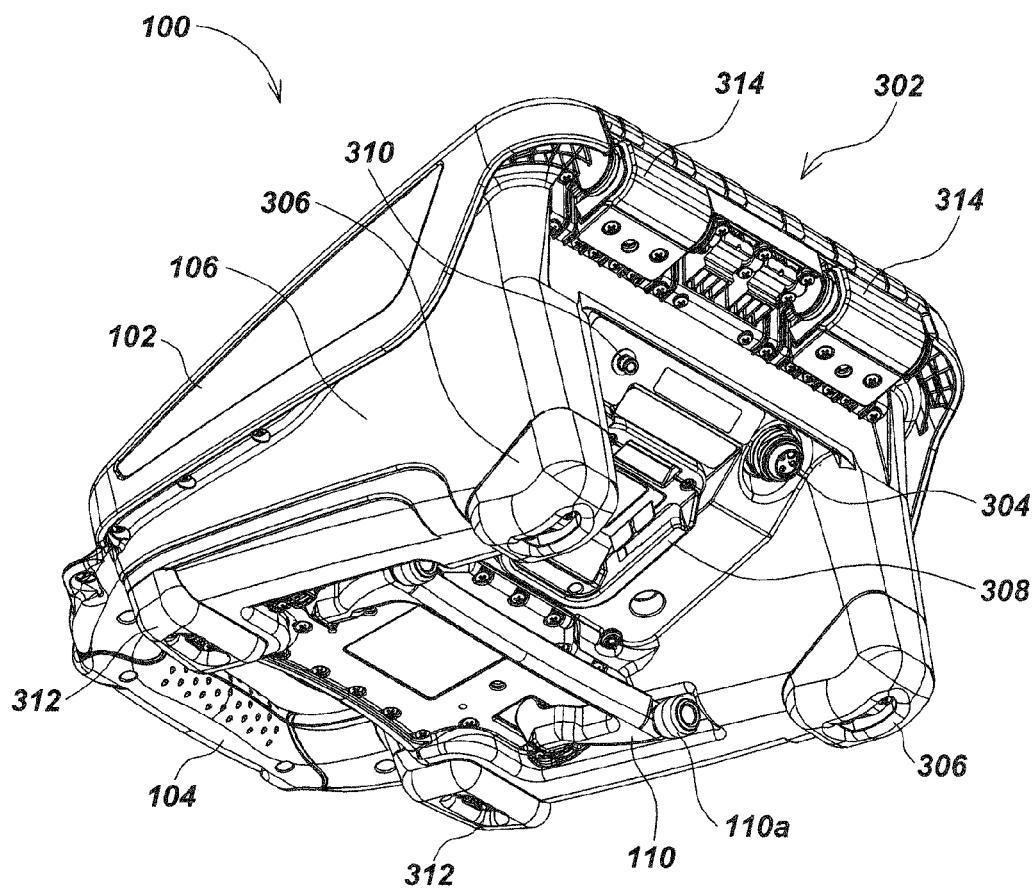
FIG. 3 is a bottom view of the camera controller embodiment of FIG. 1A.

Turning to FIG. 3, camera controller embodiment 100 may include a hinge assembly 302 for robustly attaching protective cover 102 to the case 106. Hinge assembly 302 may include rubber or plastic molded bumpers 314.

The camera controller may be fitted with a primary signal connector, such as system cable connector 304, for example, to electrically connect the camera controller 100 to a pipe-inspection system cable or, for example, to a push-cable. An embodiment of the camera controller's conductive kickstand 110, with two attached conductive-rubber feet 110a, is shown in FIG. 3 in its secured position. The camera controller may be fitted with a plurality of molded rear feet 306 and molded front feet 312 which may be formed of conductive rubber or other conductive materials and which may be internally grounded (connected to ground) in order to augment a grounding circuit.

A power receptacle 308 may be formed into the case 106 and fitted with appropriate connectors for retaining a removable battery such as a lithium-ion rechargeable battery or the like, for example. The camera controller 100 may include an internal battery for data retention when a power source is unavailable. The camera controller 100 may be fitted with an output signal connector, such as an external transmitter lug 310, to enable the associated push-cable to be energized by an external transmitter used to energize the push-cable at one or more selected frequencies for tracing with a locator receiver. Camera controller 100 may include an internal transmitter circuit for generating and providing one or more selected frequencies onto the connected push-cable for tracing when desirable. The internal transmitter may be configured to provide multiple output frequencies, such as, for example, by providing output frequencies transmitted in a timed sequence as described in U.S. Patent Application Ser. No. 61/607,510, filed Mar. 6, 2012 entitled DUAL SENSED LOCATING SYSTEMS AND METHODS, the entire content of which is incorporated by reference herein.

The rear molded feet 306 and the hinge-cover bumpers 312 may be installed in such a way as to allow the unit 100 to stand stably either horizontally or on end.

Figure 4:
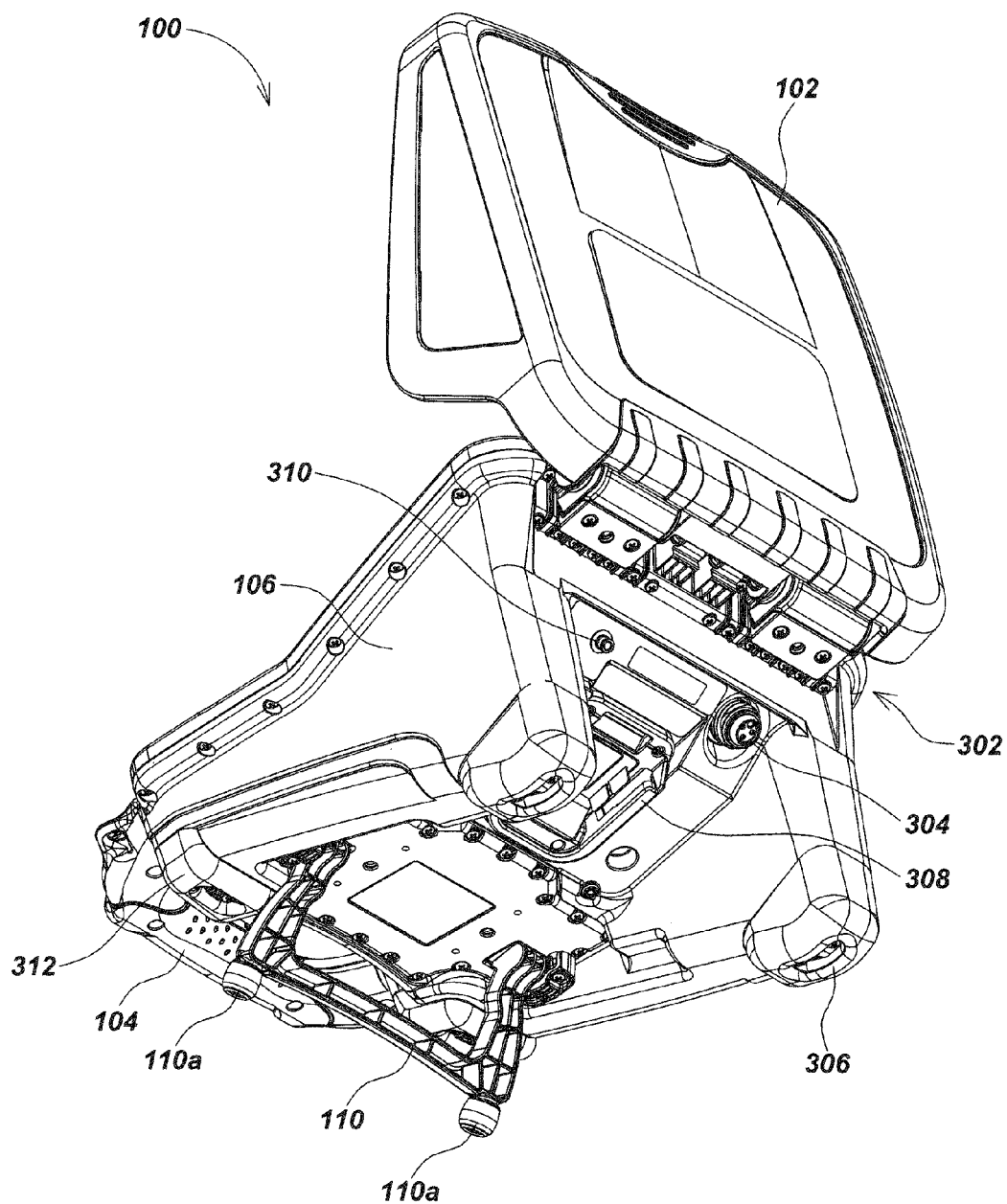
FIG. 4 illustrates details of the camera controller embodiment of FIG. 1A, taken from the underside thereof.

Turning to FIG. 4, the camera controller embodiment 100 is shown from below with the kickstand 110 deployed. The interior of the case 106 or parts thereof may be treated with an applied layer of conductive paint or other conductive surfaces or materials which, in conjunction with the conductive-rubber feet 110a, may provide a grounding path when an internal transmitter in the camera controller 100 is engaged to energize a pipe-inspection push-cable, for example, at one or more chosen frequencies. Conductivity for the ground path may be augmented by interior plating or the addition of other conductive elements, for example, in the interior of case 106.

Figure 5:
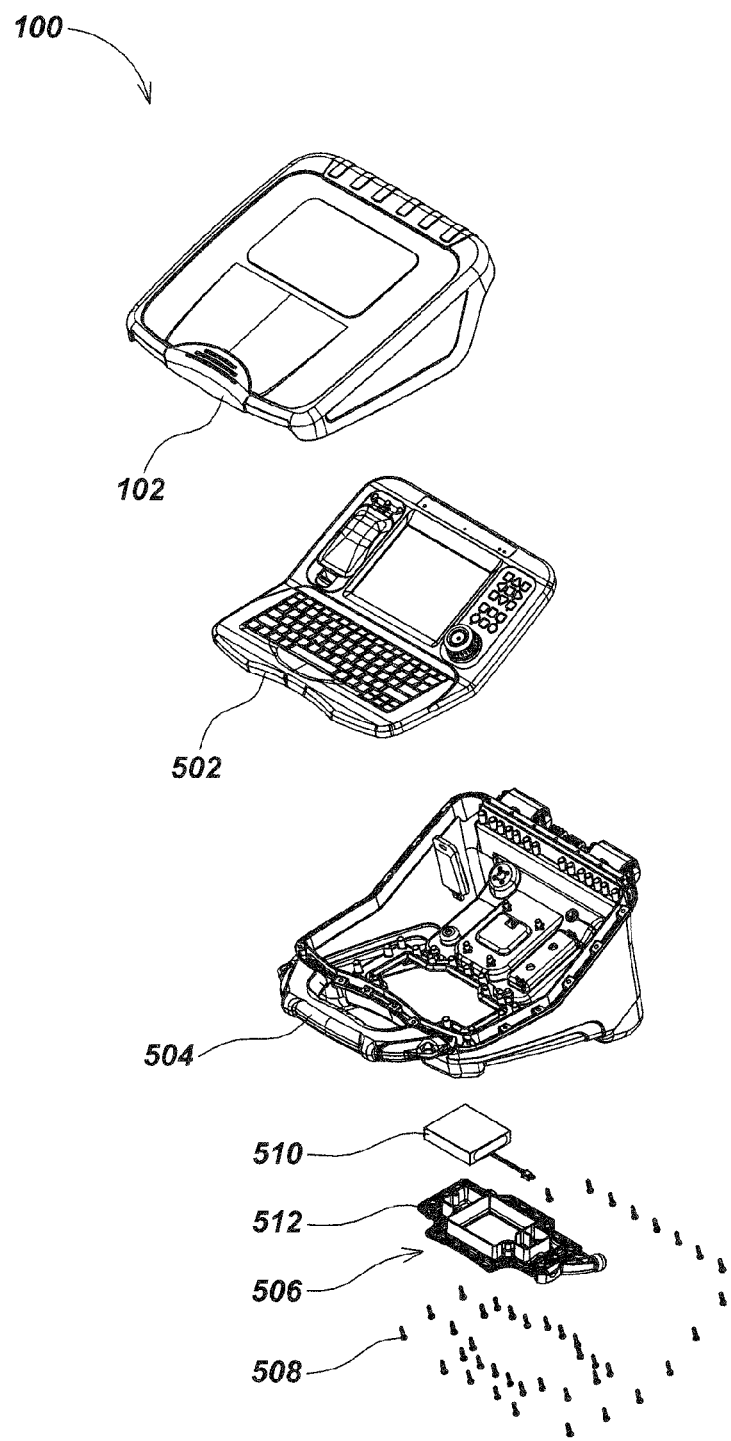
FIG. 5 is an exploded view of the camera controller embodiment of FIG. 1A.

Turning to FIG. 5 the camera controller 100 may comprise protective cover 102, a control panel assembly 502, a case assembly 504, and a kickstand assembly 506. A plurality of screws 508 such as, for example, Plastite, or similar screws, may be used to assemble the complete controller 100 from the various sub-assemblies described. The internal battery 510 may be seated in a raised section of the access plate 512.

Figure 6A:
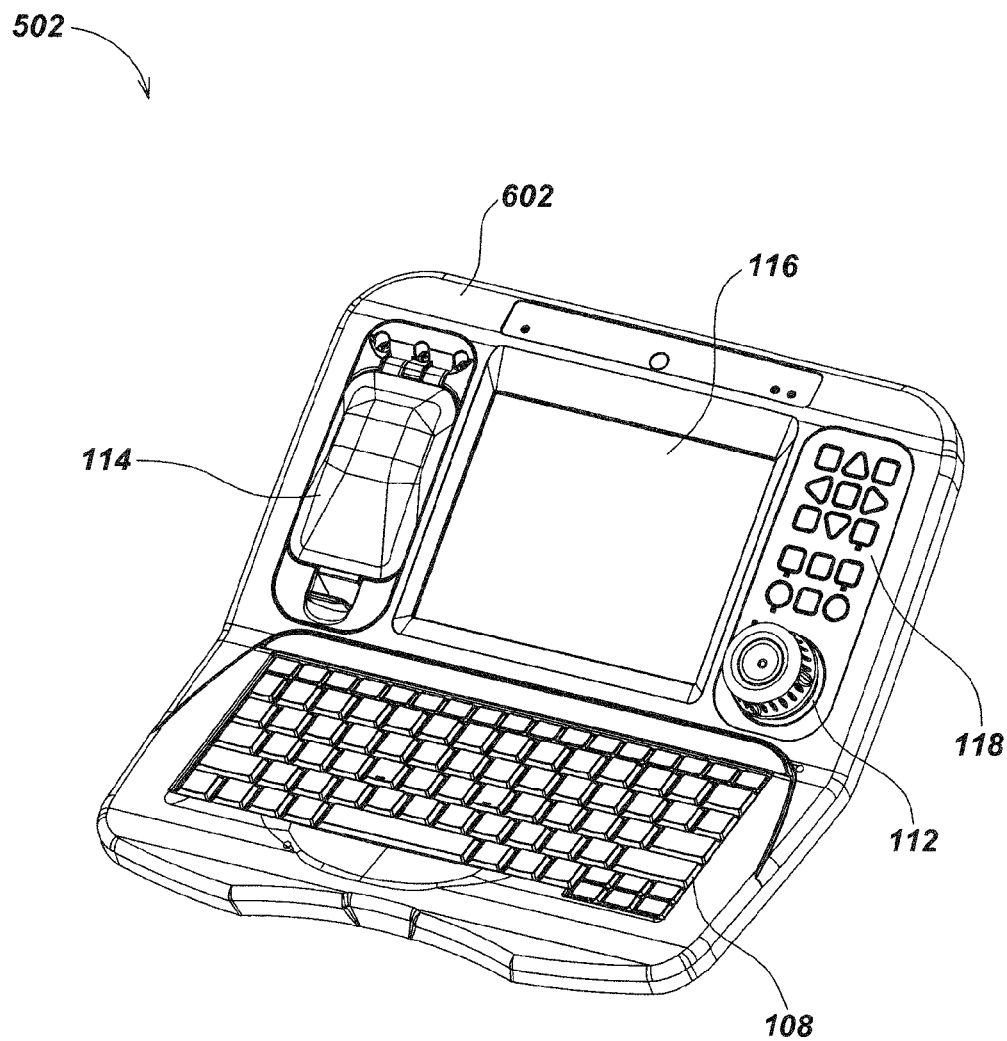
FIG. 6A illustrates the control panel assembly of the camera controller embodiment of FIG. 1A.

Referring to FIG. 6A, the camera controller's may include a control panel such as control panel assembly 502 which may comprise, for example, a front panel case 602 which may support the keyboard 108, a magnetic user interface device such as a magnetic mouse as described in the incorporated applications and/or and joystick 112, the port cover 114 protecting a plurality of USB ports, the display screen 116, the control keypad 118, and/or other user interface elements (not shown).

The USB ports may be of varied depths enabling them to accept larger-capacity removable drives as described in the U.S. patent application Ser. No. 13/346,668, entitled PORTABLE CAMERA CONTROLLER PLATFORM FOR USE WITH PIPE INSPECTION SYSTEM, filed on Jan. 9, 2012 and U.S. patent application Ser. No. 13/774,351, entitled DOCKABLE TRIPODAL CAMERA CONTROL UNIT, filed Feb. 22, 2013, incorporated by reference herein their entirety.

Figure 6B:
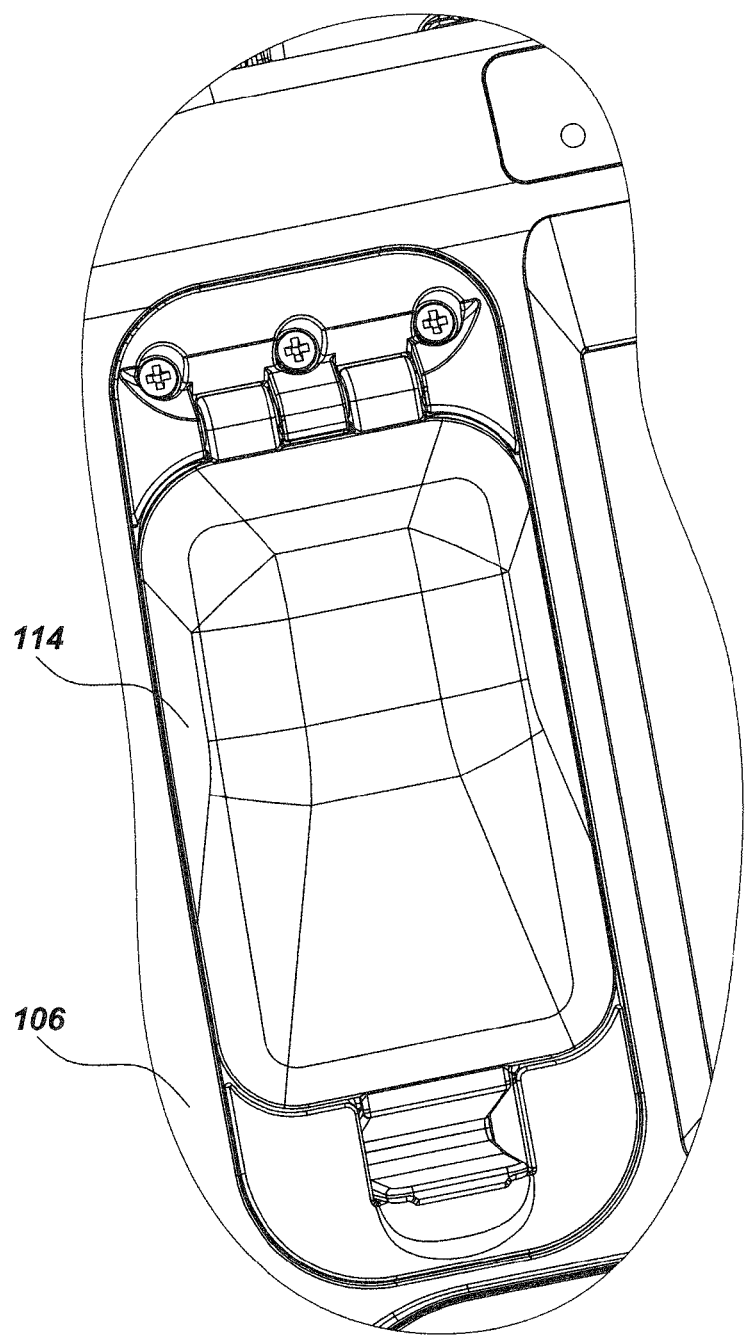
FIG. 6B illustrates details of the connector port with the port cover closed.
Figure 6C:
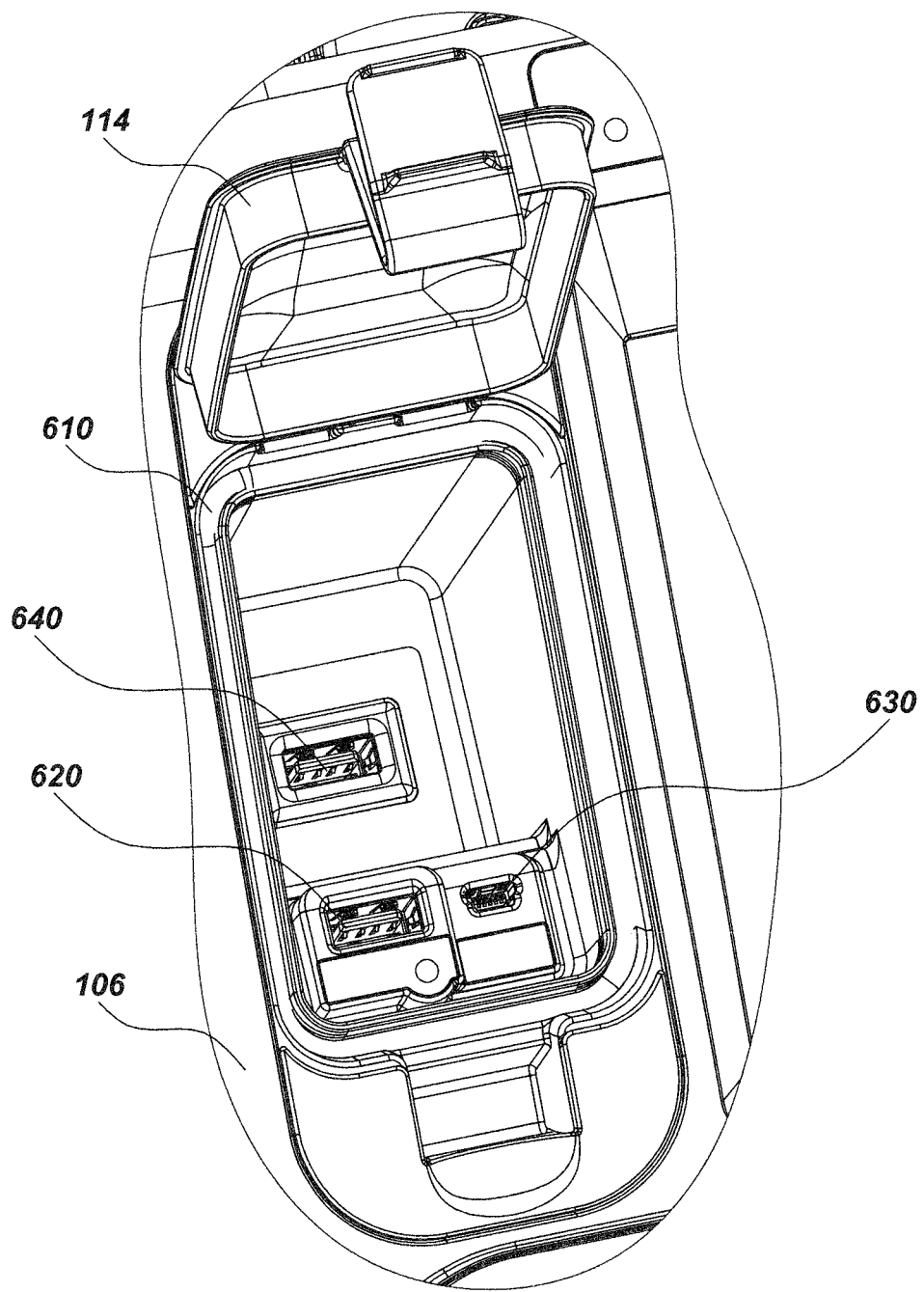
FIG. 6C illustrates details of the connector port with the port cover open.
Figure 6D:
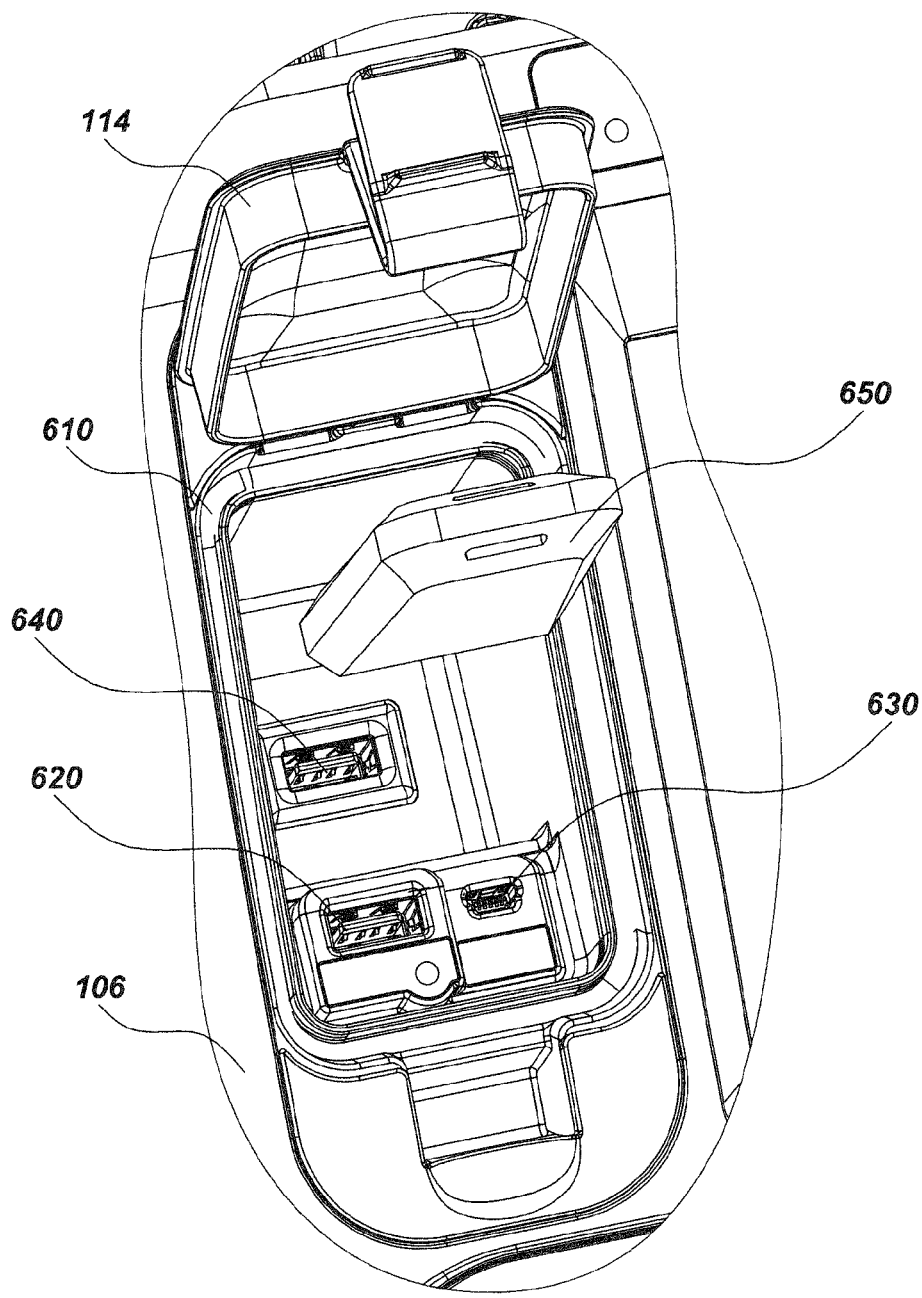
FIG. 6D illustrates a USB drive with the stepped down terminal within the connector port.

As illustrated in further detail in FIGS. 6B-6D, as the port cover 114 is opened, a port seal 610 and various ports or connectors may be revealed. The port seal 610 may protect internal ports from moisture and debris. A USB port 620, mini USB port 630, and stepped down USB port 640 may exist in the connector port. The stepped down USB port 640 may be located deep enough within the connector port to allow a removable USB drive, such as thumb drive 650 of FIG. 6D, to be connected and still allow the port cover 114 to close thus providing protection to the removable USB drive within. In alternative embodiments, various other port or connector types may be included.

Figure 7:
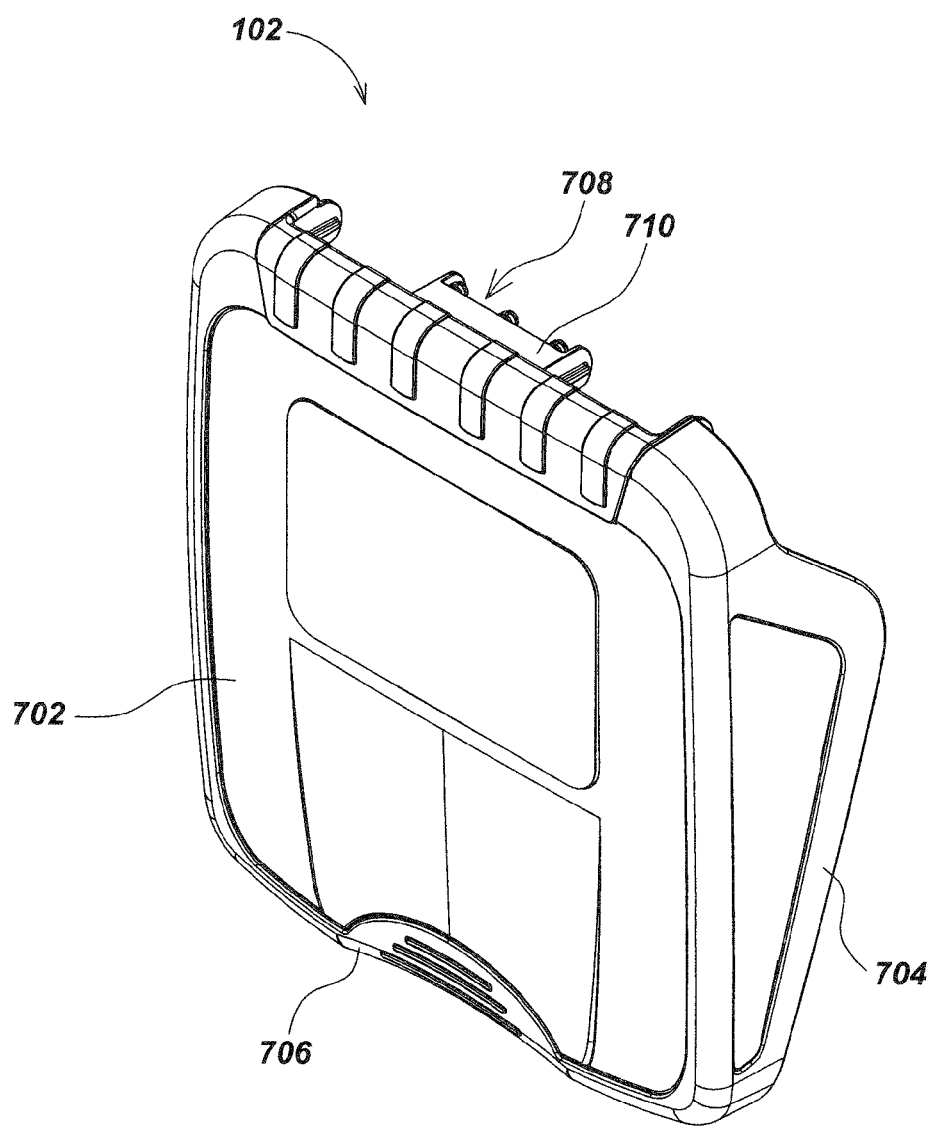
FIG. 7 illustrates the cover and sunshade of the camera controller embodiment of FIG. 1A.
Figure 8:
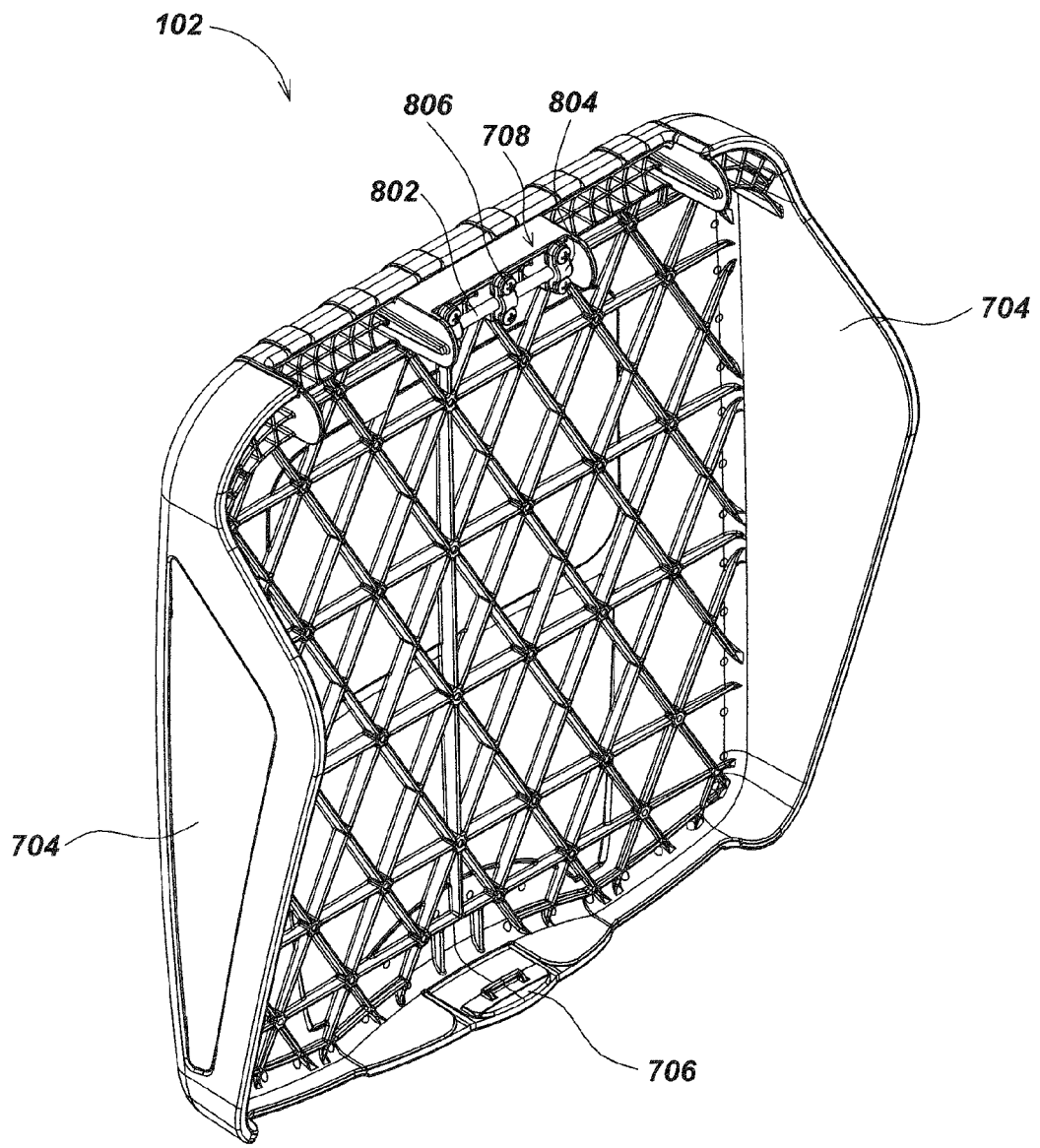
FIG. 8 is an bottom view of the cover and sunshade.

Referring to FIGS. 7 and 8, the protective cover 102 may include a cover top section 702, formed with two cover side panels 704, a molded cover latch 706, and a cover hinge assembly 708, which may include a cover hinge dowel pin 802 retained by cover hinge dowel clamps 804 and one or more fasteners, such as screws 806 that may be secured into a hinge feature 710 formed onto the protective cover 102.

Figure 9:
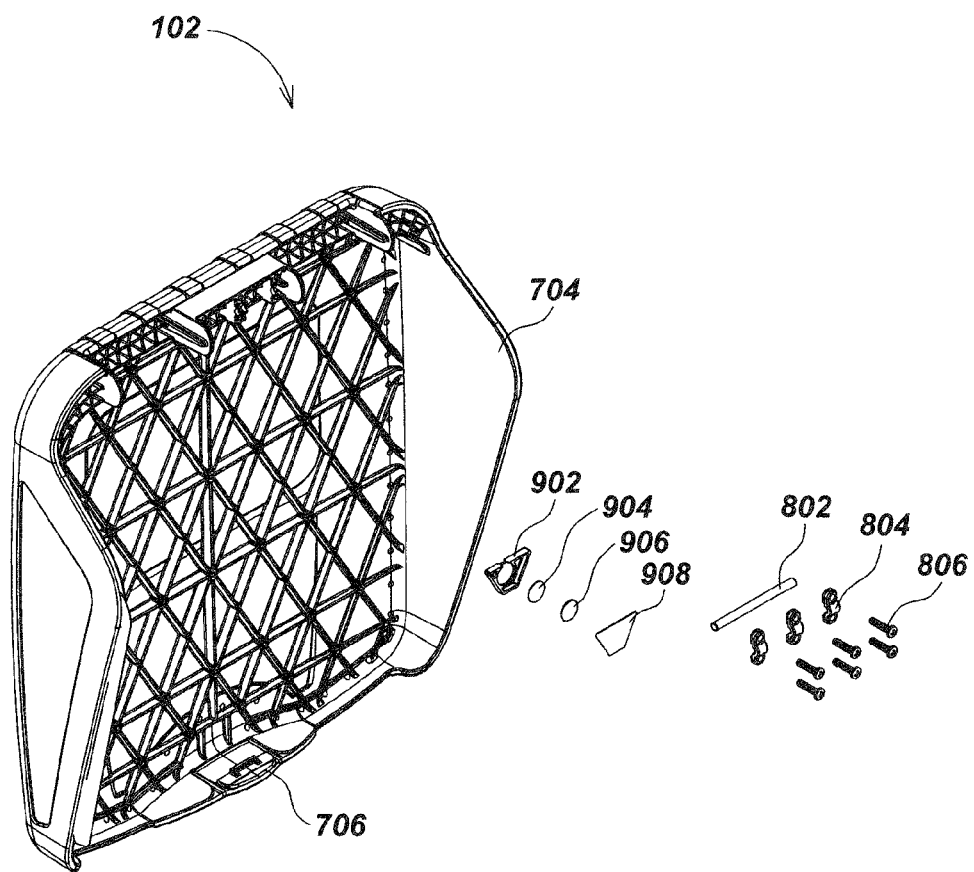
FIG. 9 is an exploded view of the cover and a sense magnet assembly.

Referring now to FIG. 9, in one aspect the camera controller cover 102 may include a magnet retaining form 902 into which a layer of double-sided tape 904 may be fitted to secure a magnet, such as a circular neodymium magnet 906. The magnet 906 may include a label 908. The movement of the magnet 906 may be detected by magnetic sensors, such as sensors incorporated into an electronics or processing module of the camera controller. The electronics or processing module may then process the resultant signal to interpret the state of the cover, such as, for example, opened, closed, opening, closing, etc. Such signals may be used in software in a processing element to, for example, allow the camera to sleep in a power-save mode or to wake from a power-save mode at appropriate times depending on the state of the cover.

Figure 10:
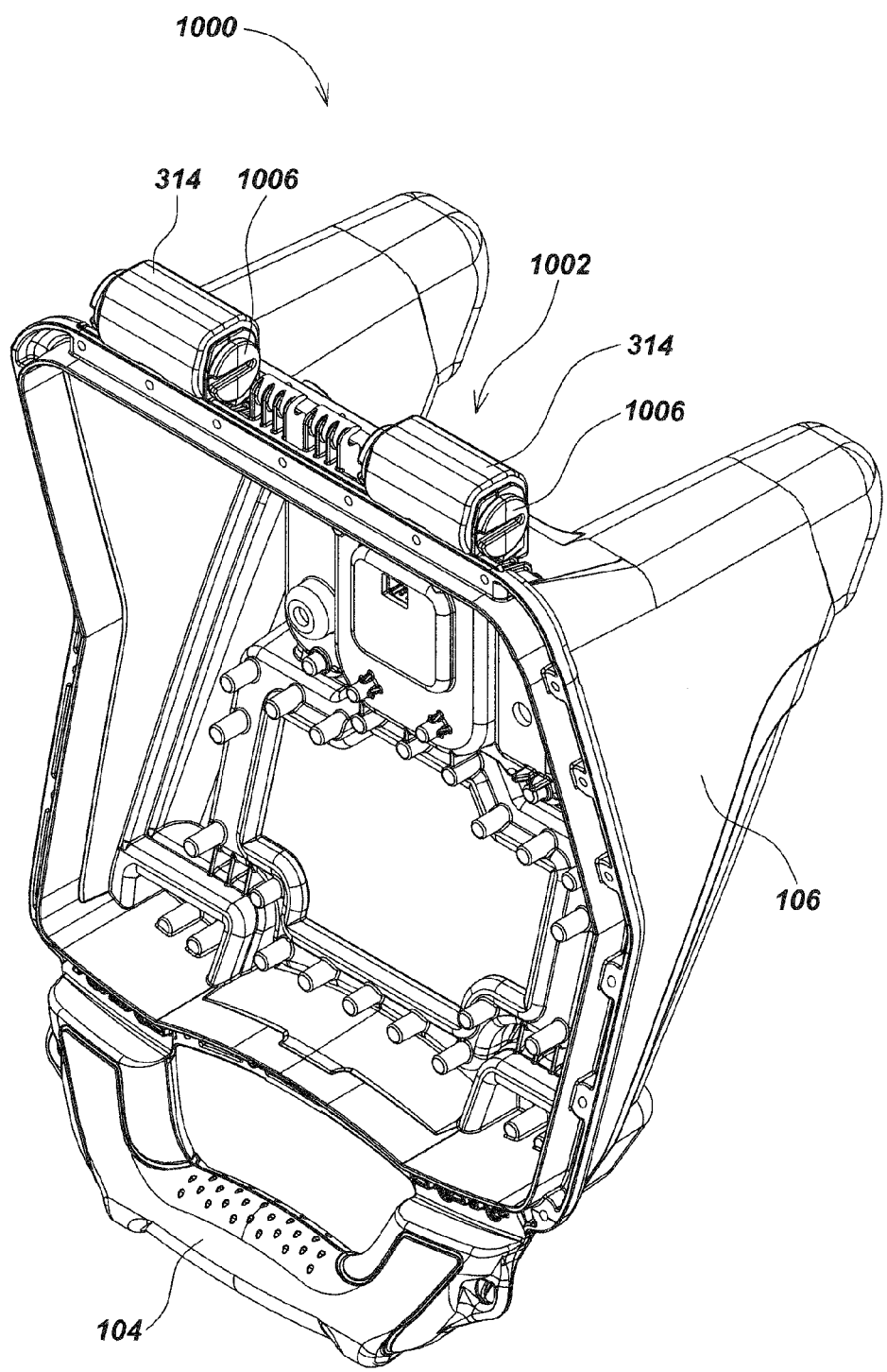
FIG. 10 is a perspective view from above of the lower case of the camera controller embodiment of FIG. 1A.
Figure 11:
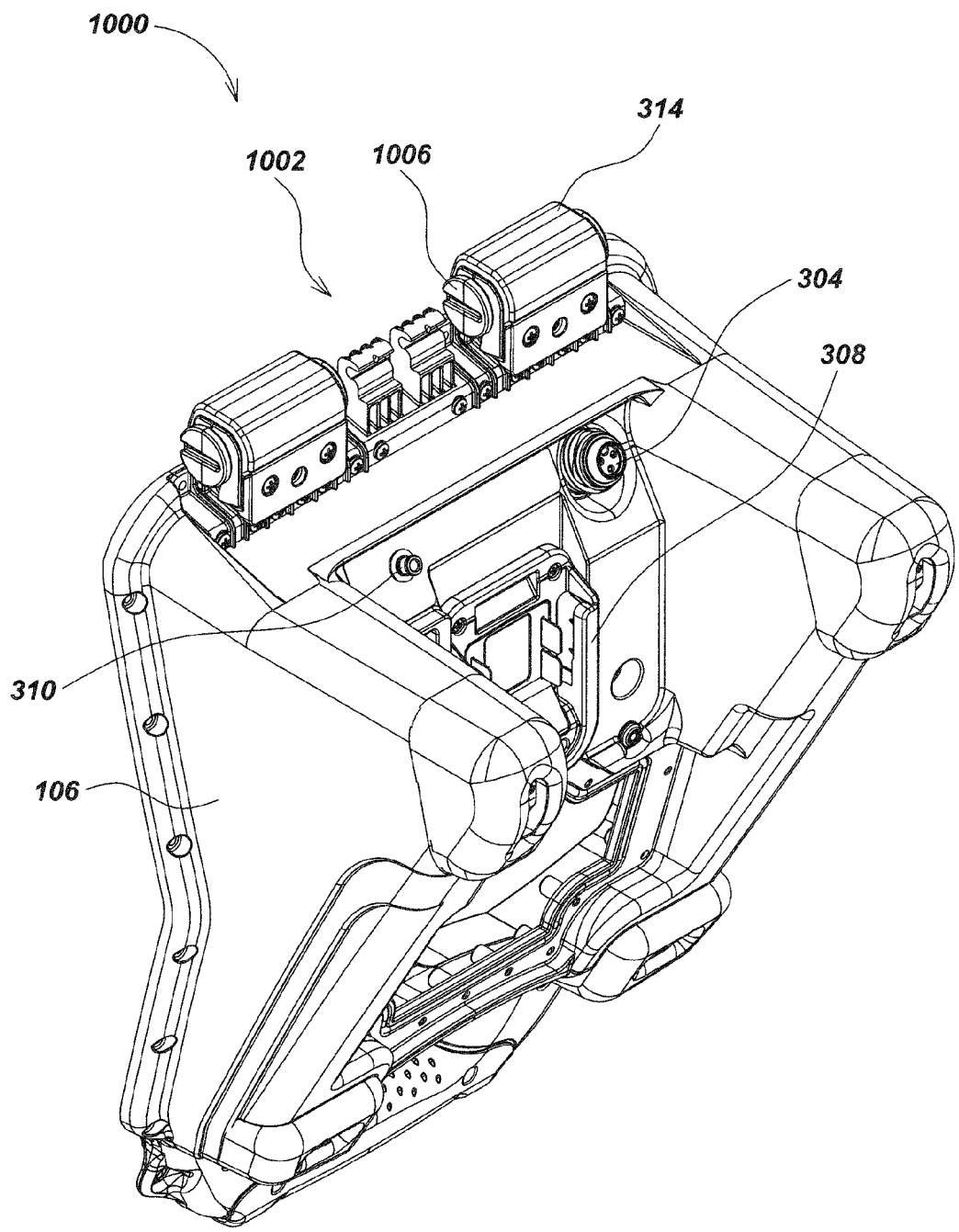
FIG. 11 is a perspective view from below of the lower case and hinge assembly of the camera controller embodiment of FIG. 1A.

Referring to FIGS. 10 and 11, the camera embodiment 100 may include a lower housing or case assembly, such as lower case assembly 1000, which may include a molded case 106 as shown. The case may include a hinge element, such as case hinge assembly 1002, which may be protected by two plastic formed bumpers 314 each of which may cover a hinge assembly. Each hinge assembly may include a formed torsion rod 1006 which may be cam-shaped sufficiently to provide gradually increasing friction as the case is opened.

Power may be provided by one or more removable batteries, such, for example, an 18V lithium-ion battery or other battery module that may be mounted to a battery connector 308. In addition, in some embodiments line or AC power may also be used, in which case standard power supply circuitry may be used to generate DC outputs from an AC line or other supply. A power supply module, such as a buck converter switching power supply for example, may be used to supply camera voltage and provide 8.5 to 12 volts to power the camera of the pipe-inspection system. A separate switching power supply may be used to modify the supplied power to provide voltages of 0.85V, 1V, 3.3V, and 5V, for example, to the pipe-inspection system for other powering functions. Examples of battery pack apparatus and systems as may be used in various embodiments of a camera controller, such as camera controller embodiment 100, are described in U.S. Utility patent application Ser. No. 13/532,721, entitled MODULAR BATTERY PACK APPARATUS, SYSTEMS, AND METHODS, filed Jun. 24, 2012, U.S. Provisional Patent Application Ser. No. 61/663,617, entitled MODULAR BATTERY PACK APPARATUS, SYSTEMS, AND METHODS INCLUDING VIRAL DATA AND/OR CODE TRANSFER, U.S. Provisional Patent Application Ser. No. 61/501,172, entitled MODULAR BATTERY PACK APPARATUS, SYSTEMS, AND METHODS, filed on Jun. 24, 2011, U.S. patent application Ser. No. 13/774,351, entitled DOCKABLE TRIPODAL CAMERA CONTROL UNIT, filed Feb. 22, 2013, and U.S. Patent Application Ser. No. 61/521,262, entitled MODULAR BATTERY PACK APPARATUS, SYSTEMS, AND METHODS, filed on Aug. 8, 2011. The content of each of these applications is incorporated by reference herein in its entirety. In some embodiments a camera controller, such as camera controller embodiments 100, may include a processing element configured to provide viral data and/or code transfer to and/or from coupled devices as described in incorporated patent application Ser. No. 61/663,617 so as to allow transfer of data and/or code to coupled battery packs and/or to send data and/or code to coupled battery packs.

Figure 12:
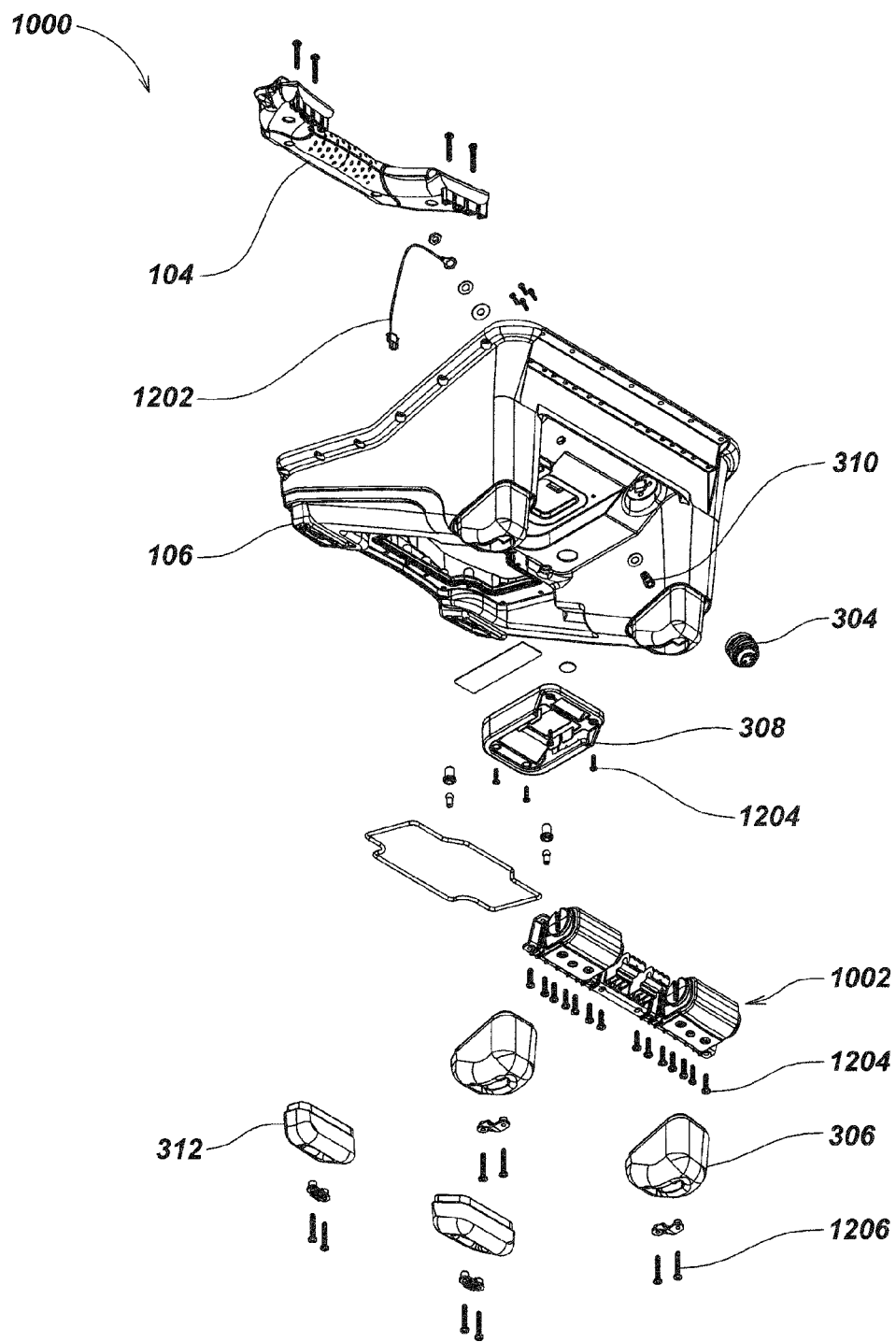
FIG. 12 is an exploded view of the lower case of the camera controller embodiment of FIG. 1A.

Referring to FIG. 12, an exploded rear view of the lower case assembly embodiment 1000 illustrates the lower case 106 with its associated carrying handle 104. A conductive cable 1202 may be used to connect the transmitter lug 310 to the circuitry used to energize a pipe inspection push-cable connected by means of the system cable connector 304 and an associated cable drum. Battery connector 308 may be attached to the lower case 106 using fasteners or other connecting elements, such as screws 1204. Lower case hinge assembly 1002 may likewise be attached to lower case 106 with screws 1204, for example. Molded rear feet 306 and front feet 312 may be formed of conductive rubber or other conductive materials and may be internally connected electrically to provide a ground return path used by a built-in transmitter. Molded feet may alternately or additionally be attached with conductive fasteners, such as conductive screws 1206. Such a ground path may be augmented by the use of conductive paint, plating or other conductive elements in selected areas of the interior of lower case 106. In one aspect of the current disclosure, the combination of capacitive and conductive grounding elements may enable a built-in transmitter to function to provide electrical coupling to the ground or other surfaces without using a separate traditional grounding stake.

Figure 13:
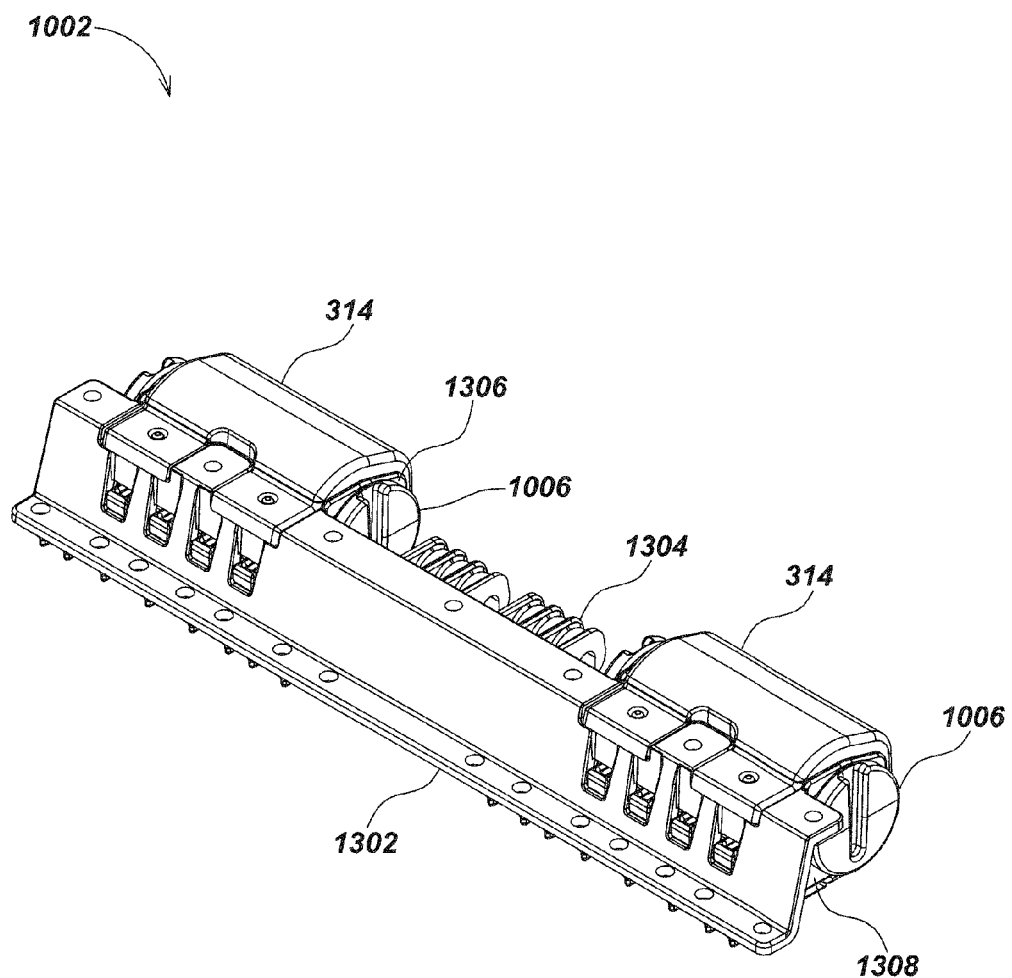
FIG. 13 and FIG. 14 illustrate details of the hinge construction of the camera controller embodiment of FIG. 1A.
Figure 14:
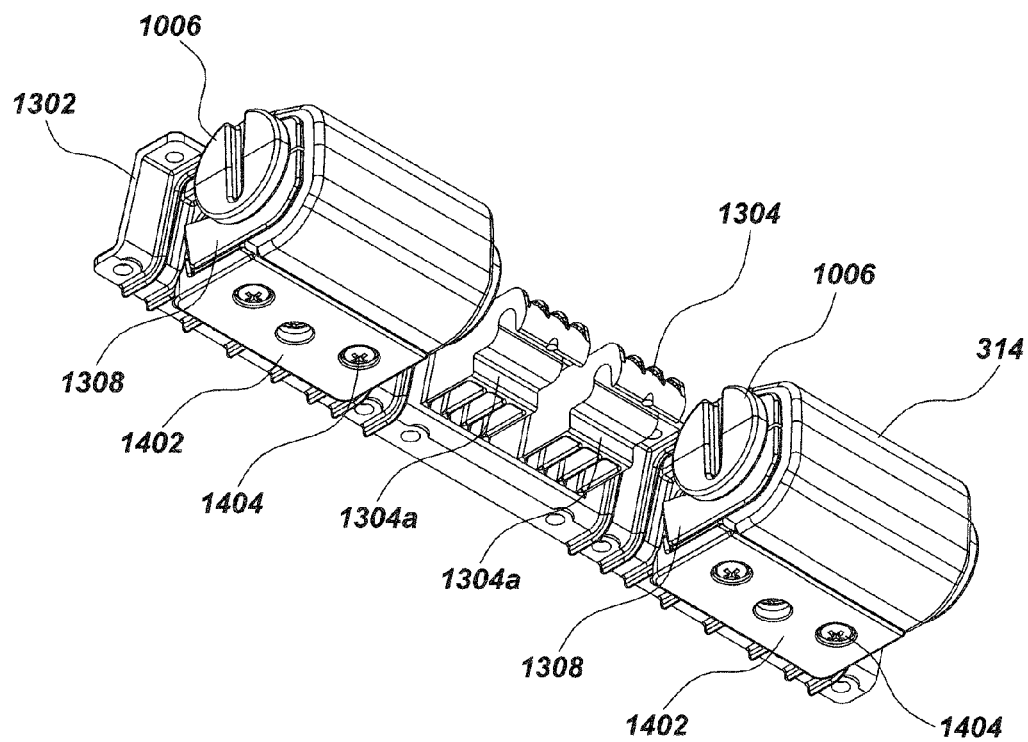
Figure 15A:
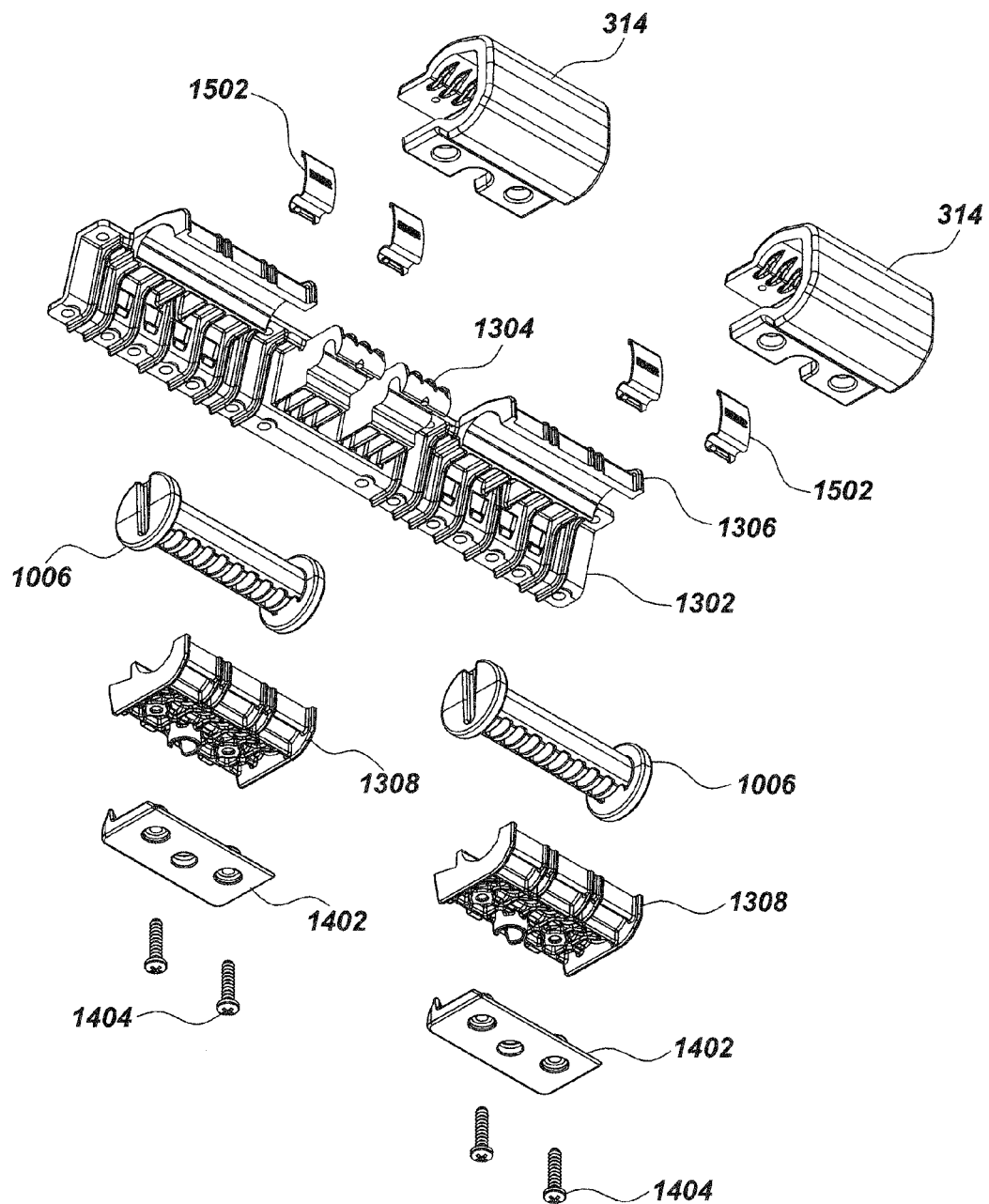
FIG. 15A is an exploded view of the hinge assembly of the camera controller embodiment of FIG. 1A.

Referring to FIGS. 13, 14, and 15A, in an exemplary embodiment the case hinge assembly 1002 may include a case hinge backing structure 1302, which may be formed with a plurality of upper dowel supports 1304 and formed upper torsion rod cam supports 1306. The upper dowel supports 1304 may be formed with a cover stop features 1304a which may aid in removing the protective cover 102 (FIG. 1). A torsion rod cam 1006 may seat against backing structure 1302 under each upper torsion rod cam support 1306, and may be secured by a lower cam support plate 1308 and a bumper 314, a bumper cover 1402 and screws such as 1404. The lower cam support plate 1308 may further be joined to the upper torsion rod cam support 1306 by means of a plurality of spring clips such as 1502, for example. Each of the bumpers 314 may be formed to fit snugly around a torsion rod cam 1006 and the torsion rod cam upper support 1306 and lower support 1308. As best illustrated in FIG. 15B, the form of the hinge supports may allow the protective cover 102 to be firmly held by friction when open, but to be released and removed from attachment when pushed past the fully open position. At a fully open position as shown, hinge feature 710 of the protective cover 102 may contact the cover stop features 1304a. Additional applied force may allow cover hinge dowel pin 802 (FIG. 8) and thereby the protective cover 102 to be freed from the upper dowel supports 1304 (FIG. 13) and lower case 106. Such a design acts as a fail-safe to prevent breakage in the event of accidental force being applied to the top in its open position, for example, and allows a user to remove the protective cover 102 if desired.

Figure 16:
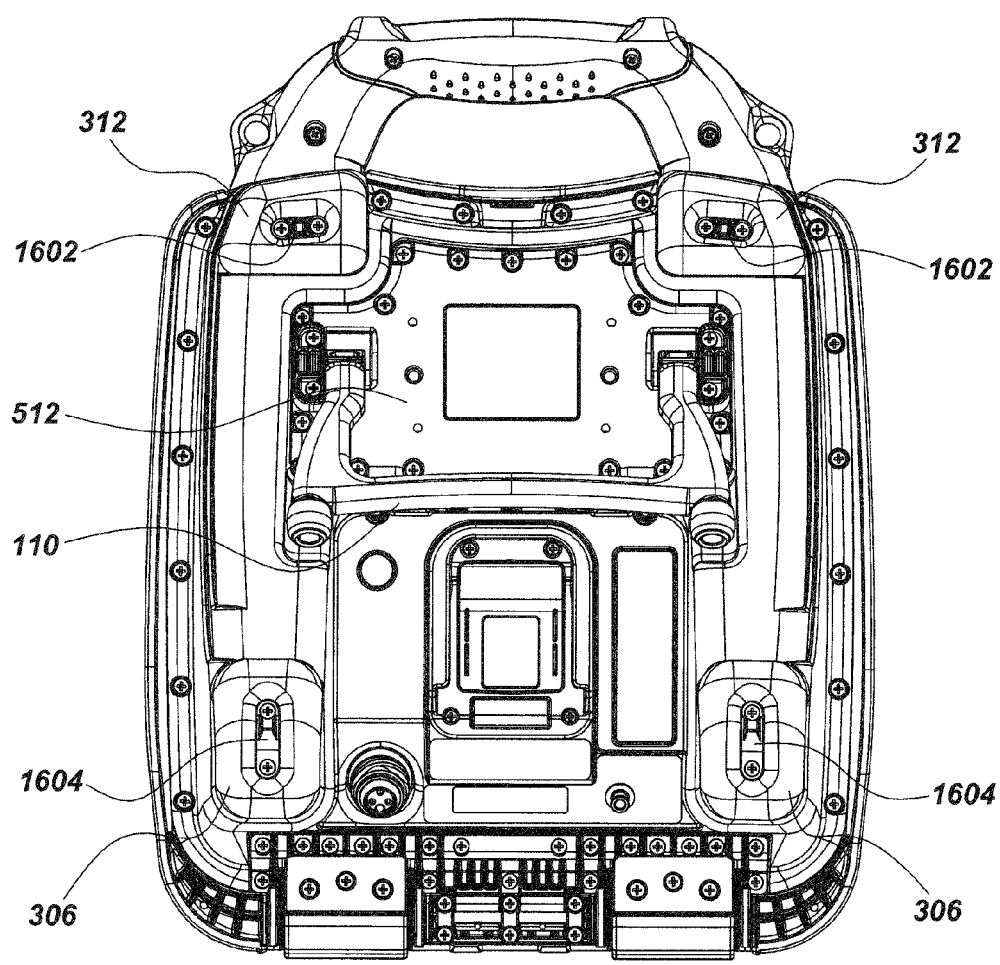
FIG. 16 illustrates details of the camera controller embodiment of FIG. 1A, taken from the underside thereof.

Referring to FIG. 16, the molded rear feet 306 may each be attached using a conductive retainer 1604 or other conductive element, and the molded front feet 312 of conductive rubber may each be attached using conductive retainer 1602 or other conductive element to assist in the grounding path used when the built-in transmitter is active. Additionally the kickstand 110 may be formed of conductive plastic or other materials, for example, for the same reason. The grounding path may be further assisted by the use of a metallic or other conductive material plate, such as an aluminum access plate 512, for example, connected to the kickstand 110. Grounding path conductivity may be augmented with the application of conductive paint or other conductive materials disposed on the interior of lower case 106, by plating, or additional conductive elements. In one aspect, an internal battery 510 (FIG. 5) may be seated behind the access plate 512 connected electrically to the removable battery so that the internal battery may be recharged by the external battery.

Figure 17:
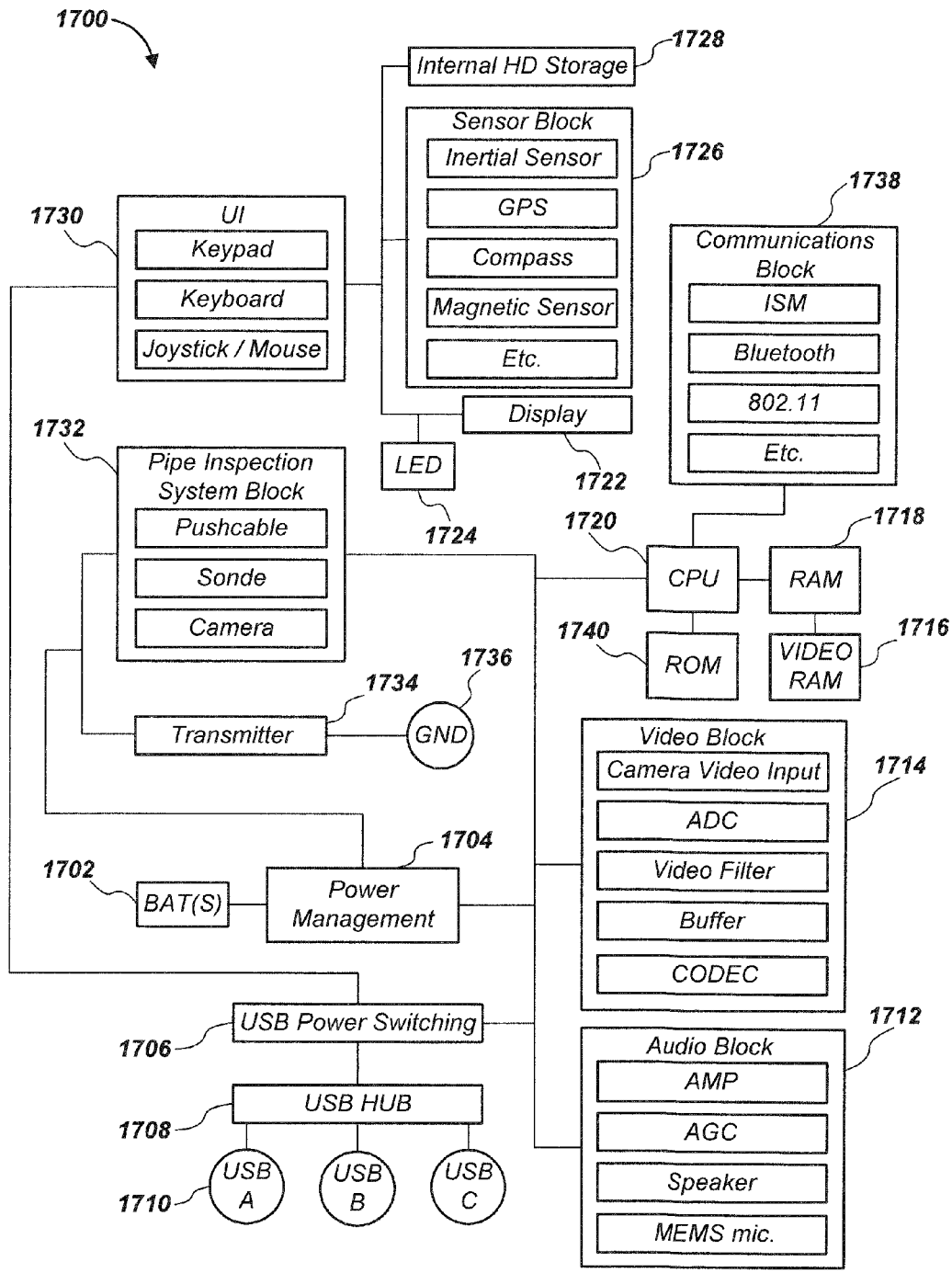
FIG. 17 is a block diagram of power connections for a typical embodiment of a camera controller.

Turning to FIG. 17, a block diagram of power management connectivity in an exemplary system embodiment 1700 illustrates connectivity from, for example, 18V Lithium-ion battery 1702 via a power management block 1704, which may be a dedicated PCB or part thereof, for example. Power management block 1704 may control power supply to a USB switching circuit 1706 and associated USB hub 1708 which may drive a plurality of USB ports 1710. A separate audio block 1712 with associated amplifier, gain control, microphone control and speaker may be similarly powered under the control of the power management block 1704. Power management block 1704 may control power required for the video block 1714, which incorporates camera, video ADC circuits, video buffers and filters and the digital CODEC processes, which may be controlled by software operations through the CPU 1720. A video RAM 1716 and a system RAM 1718, as well as access to a read-only memory (ROM) 1740 may be powered under control of the power management block 1704. Additional power distribution governed by the power management block 1704 may include a camera controller system display 1722, one or more system status LEDs 1724, one or more sensors 1726, which may include GPS, orientation detection, and inertial sensors, magnetic sensors, for example. Data storage on, and operation of, one or more internal hard disks 1728 may be included in the power distribution scheme. An internal hard-disk storage device 1728 may be a solid-state device, such as a Winchester disk device, for example, or of some other similar device.

Power required by a user interface block 1730, which may include a keypad, a mouse, a keyboard, a joystick or similar devices may also draw on power from the battery 1702 under control of the power management block 1704. In one aspect, power management block 1704 may govern power demands for the pipe inspection block 1732, which may include the camera, sonde. And/or push-cable data transmission. When activated, a built-in transmitter 1734 may also be powered by the 18V battery 1702 under control of the power management block 1704. The built-in transmitter 1734 may use the structural grounding path 1736 as described above to complete its circuit.

Buck convertors or other voltage regulation devices or schemes may be used to provide appropriate voltages, for example, to camera, speakers, and devices where voltage requirements may vary.

Figure 18:
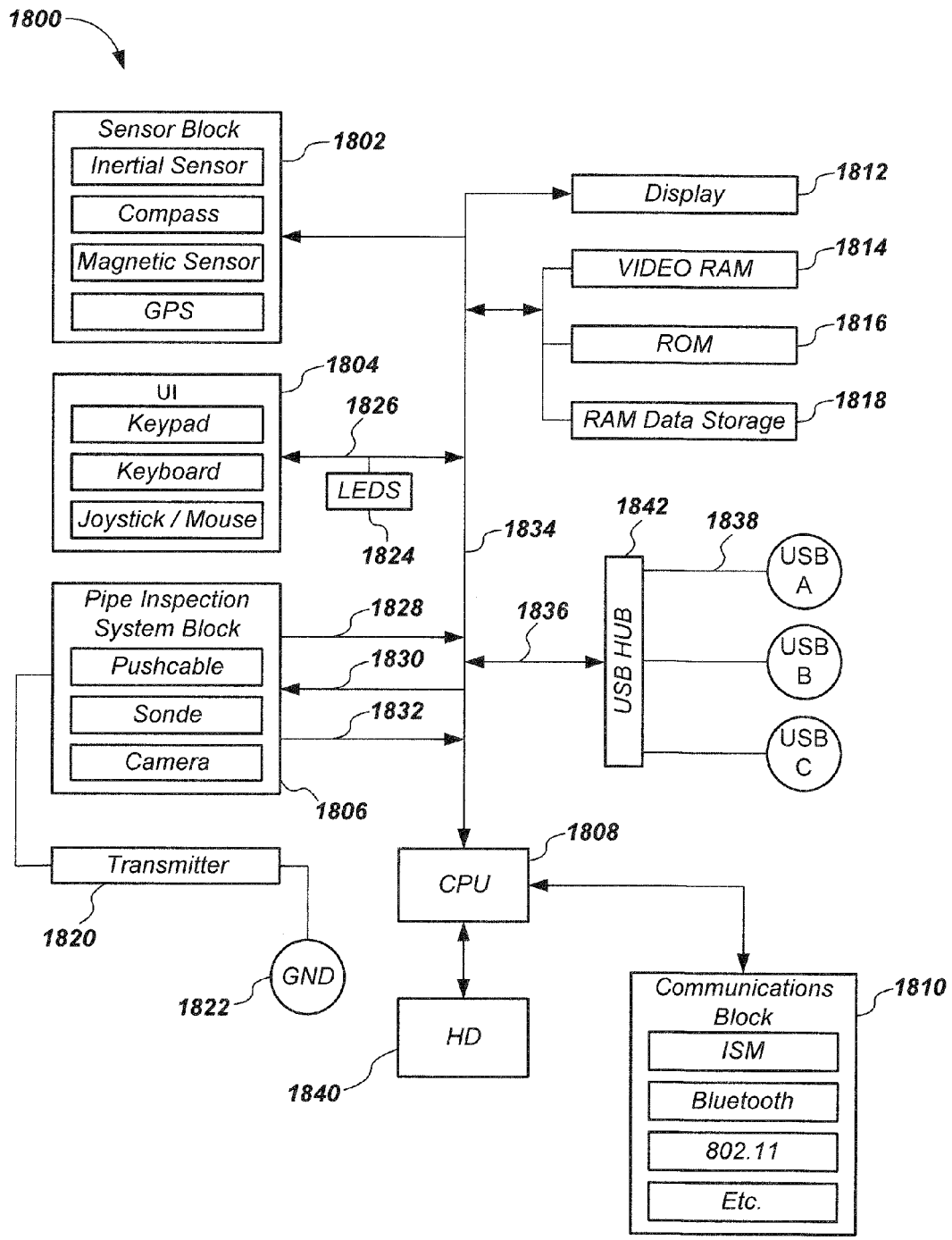
FIG. 18 is a functional block diagram of the camera controller.

Turning to FIG. 18, a functional block diagram of an exemplary camera controller embodiment 1800 is illustrated. A sensor block 1802 may include, for example, inertial sensors such as accelerometers, compass sensors, a GPS receiver capable of processing received GPS/GLONASS signals, magnetic sensors, and/or other position, location, motion, and/or acoustic/audio sensors depending on the particular application intended. In an alternative embodiment in which the pipe inspection camera may itself be equipped with inertial, positional, or acoustic sensors, for example, the input received from such sensors may be processed along similar channels as those shown for sensor block 1802.

One or more user interface functions 1804 may include, for example, an input keyboard, a control keypad, a joystick, a mouse, or combinations thereof. In an exemplary embodiment, a magnetically sensed user interface device as described in the incorporated applications may be used. Other forms of user input such as touch pads, wirelessly linked tablets or specialized input devices may also be used.

Figure 19:
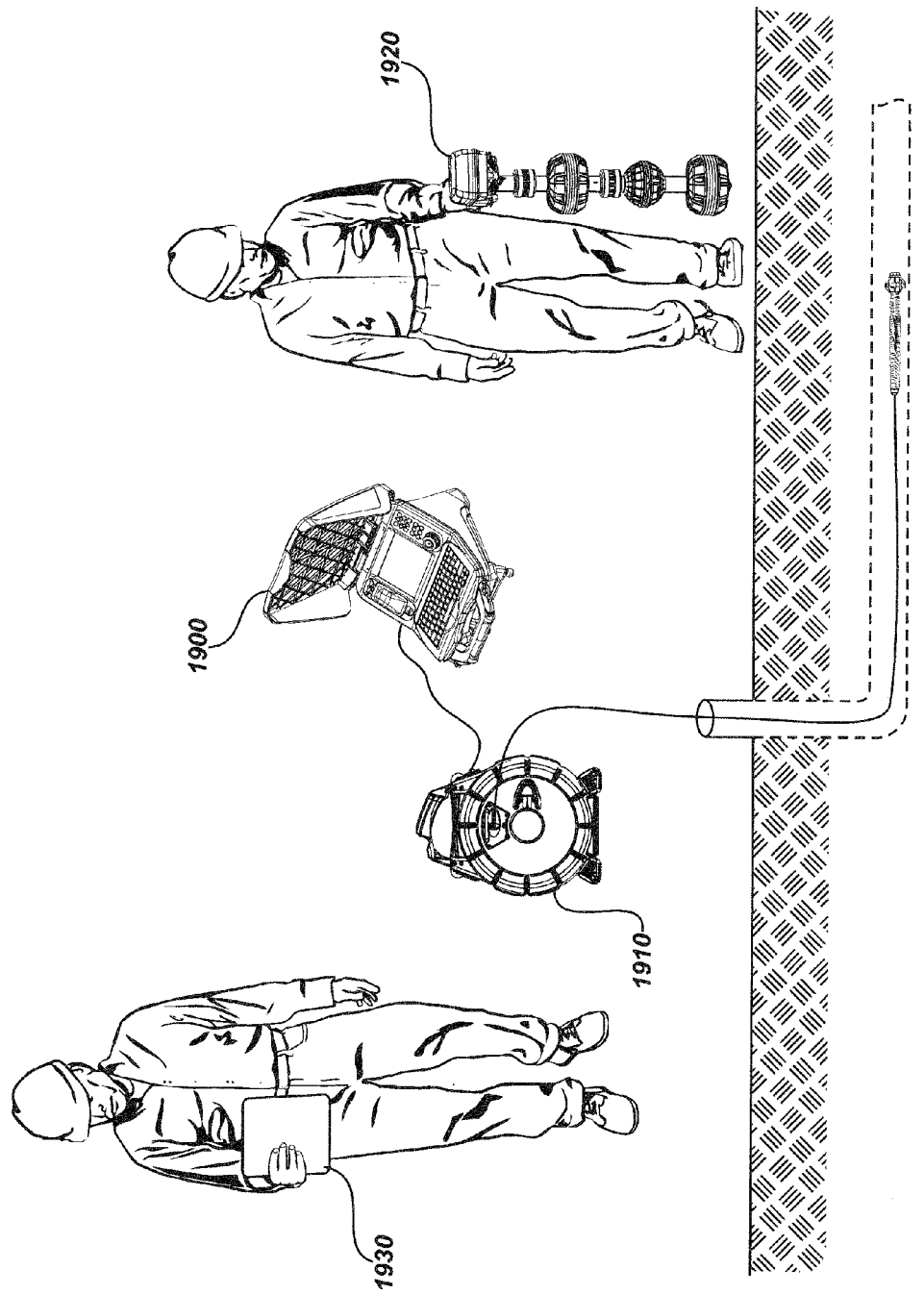
FIG. 19 is an illustration of an embodiment in use with a locator device and tablet computer device.

Turning to FIG. 19, a camera controller embodiment in keeping with the present disclosure, such as the camera controller 1900, may be enabled to communicate and operate with a variety of peripheral devices and systems. Some of these peripheral devices and systems may include, but are not limited to, pipe inspection cameras 1910, utility locator devices 1920, and mobile computing devices 1930, for instance smart phones and/or tablet computers.

A pipe inspection block 1806 may be used to transmit data from camera, lights, and sonde, as well as other sensors associated with the pipe inspection camera, to a CPU 1808 by way of a data bus 1834. Data relay from a communications block 1810 may include, for example, ISM data links to a locator, data receipt from remote devices such as beacons, locator or transmitters, WLAN connectivity to remote processors, or the like. Under control of CPU 1808 display data may be processed, stored in video RAM 1814 for local display 1812, and may be routed to the communications block 1810 for relay to remote displays, for example. A locator receiver, for example, may be configured to receive camera images from camera controller 1800 via an ISM or other wireless link. Non-volatile instructions, such as, for example, boot sequence, may be stored in and retrieved from a read-only memory (ROM) 1816. Volatile data may be written to and retrieved from a random-access memory (RAM) 1818.

A transmitter device, such as a built-in transmitter 1820 capable of transmitting one or more frequencies may be activated under CPU control 1808 based, for example, on input from the UI block 1804, and used to energize the push-cable of the pipe inspection system for tracing purposes. An internal ground circuit 1822 may obviate the need for an external grounding stake when energizing the push-cable for tracing. One or more local status LEDs 1824 may show system status indications such as power state and battery level, for example.

Control data from the UI block 1804 may be transferred to the CPU 1808 by way of a control bus 1826. Sonde, camera status data, etc. may be sent from the pipe inspection system 1806 to the controller on a data bus 1828. Pipe inspection control data may be transferred via a pipe inspection control bus 1830. Video data from the system camera may be transferred via a video bus 1832. A system data bus 1834 may transfer data for the several subsystems to and from the CPU. One or more buses of the system may be physical buses, for example, or logical separations of data on common physical paths. Multiple USB ports in a USB array 1838 may be connected to a dedicated USB bus 1836 and supported by a USB hub 1842.

Under control of CPU 1808, a permanent record of camera images, sensor data, reports and templates and other operational data may be stored in memory, such as by being written to a hard disk (HD) 1840 or other memory device, which may be a solid state device, a Winchester device, or other data storage device. Under operator control, data may similarly be written to removable USB memory devices A, B, and/or C by way of USB bus 1836. For example, a report generated under software control may be written to HD 1840 and also written to a device in the USB hub 1842 for delivery to a customer.

In some embodiments of a camera controller, wireless connections between the controller and other pipe inspection system components such as the cable reel drum assembly, sondes or associated transmitters, or other pipe inspection system components or peripheral components, such as external computing systems, may be used. These connections may be implemented in place of, or in addition to USB or other wired bus connections. For example, in some embodiments, the USB connection may be replaced with a Wi-Fi, WLAN, Bluetooth wireless connection, or other wireless connection such as wireless HDMI, cellular connections, Wi-Max connections, etc., which may be implemented with wireless communication circuits or modules included in or coupled to the electronics module of the camera controller. Corresponding wireless circuits or modules may be incorporated in the cable drum assembly, such as in associated electronics components. In some embodiments, one or more cameras may be built into the camera controller in addition to the pipe inspection system's camera to provide images of the controller's environment during locate operations. Such images may be integrated in to an image-based mapping system, for example, or otherwise serve to supplement location information used during pipe inspection and location operations. Pipe inspection system data and information, such as images, video, etc., may be associated with and stored along with other data, such as positional data, other sensory data, motion data, acoustic or audio data, latitude/longitude or other coordinate data, depth data, temperature data, or other related data or information. This information may be fused or otherwise associated for further use in GIS systems, mapping systems, archival storage systems, or other systems or devices.

In some embodiments, video compression and/or decompression may be implemented to reduce the required bandwidth between various communications connections as described previously. For example, video and/or images may be compressed between the cable drum reel assembly and the camera controller electronics module and/or between the camera controller electronics module and some other electronic computing device (e.g., a notebook, laptop, tablet, smart phone, or other computer or other display or computing device), and/or between other systems. Video may be compressed by techniques known or developed in the art such as, for example, H.264, mJPEG, FLASH, wavelet compression, and the like prior to transmitting to the separate electronic computing or display device. Such a wireless mode of communication may be advantageous in that the electronic computing device/display need not be physically attached to the cable reel drum or other pipe inspection system component.

In some embodiments, a camera controller may further include a wireless network base station or hub, such as a Wi-Fi/WLAN hub, router, or hot spot to serve a live video feed for viewing in a browser on an electronic computing device or another device within the wireless coverage area. Alternately, or in addition, the camera controller may include a module for implementing other wired or wireless communications, such as an Ethernet module and port, cellular data module, and the like. The wireless network base station or hub or other communications module may be included in or coupled to the electronics module of the camera controller and/or may be included on another system component, such as the cable drum assembly.

The electronic computing device may, for example, host an HTML5 application to provide enhanced features and device controls. Any WLAN enabled device may then connect to the system and the live video would be streamed in a browser. In other embodiments, device-specific software application may be used. Additional network-related functions may include, for, example, providing a bridge function, such as via a cellular data connection or other communications link to the "Cloud" to allow a user to upload images (snapshots), video, audio, and/or reports or other data or information to a central server system or other networked system.

Network printing functionality may be included to allow the camera control unit to incorporate a printer and/or connect to a network-enabled printer to provide data or information, e.g., measurement parameters, snapshot images, or other information or data as described herein to a network enabled printer. An "auto log" function may be included to locally store data and information and automatically sync to network storage when the user (e.g., a plumber) returns to an office. In some embodiments, the camera controller may include automatic report-generating software stored on a non-transitory storage medium for execution on a processing element to create, format, store, print, correlate and/or transmit reports which integrate images, video captures, audio capture and commentary, text amendments, or other related data or information. Such software may use pre-loaded templates for such reports, for example, as may be of value to an operator for business operations, delivery to clients, or the like.

In some embodiments, a camera controller may further include a module to provide one-to-many streaming data, such as a streaming router or other streaming-capable device. In this configuration, data, such as video signals, images, audio, acoustic, or other data or information may be sent to multiple users or target devices at the same time. For example, during a home pipe inspection operation, a homeowner may be able to simultaneously view video from within their home or yard while inspecting a pipe or information may be provided to multiple users during training or demonstrations. Restrictions on the types of information accessible may be included in such a configuration, such as by providing full information to an administrator or primary user, and limited information to guest users or others.

In video display applications it may be desirable to configure the system to minimize video latency with no buffering. For example, the system may be configured to drop frames rather than buffer data to provide an impression of fast responsiveness to a user. Graphical feedback of motion may be provided when dropping video frames. For example, a fake motion blur, a moving arrow, increasing the count, or other mechanisms may be used to provide feedback to an operator to create an impression of responsiveness. Examples of embodiments of such functionality are described in the incorporated applications including, for example, U.S. Provisional Patent Application Ser. No. 61/592,524, entitled ADJUSTABLE VARIABLE RESOLUTION INSPECTION SYSTEMS & METHODS, filed Jan. 30, 2012.

In some embodiments, an auxiliary or external electronic computing device (e.g., notebook or laptop computer, tablet, smart phone, etc.) may be configured to provide additional functionality, such as controlling status and feedback for sondes, lights (e.g., lighting deployed within pipes or other cavities, transmitters, actuators, gas or liquid sensors, additional microphones or other audio or ultrasonic capture devices, and the like. Information such as battery status, memory or storage device (e.g., USB thumb drive, compact flash, SD, or other data storage device) capacity or remaining storage space, component failures or status information, or other parameters may likewise be shared between the electronic computing device and the camera controller/electronics module(s).

In various embodiments, additional and/or alternate elements and features may be implemented. For example, in some embodiments a joystick, mouse, magnetically sensed user interface device (UID) or other user interface device may be used to provide traction manipulation/control, such as to provide forward or backward movements, turns, side to side movements, and the like. These devices may also be used to provide other functions such as cursor movements or display field selection and manipulations, image manipulations and digital articulations, such as within images or video streams or within stitched images or videos, zoom functions, pan functions, tilt functions, and/or other camera view manipulations. The camera views may be digitally articulated in some embodiments such as is described in, for example, U.S. patent application Ser. No. 13/774,351, entitled DOCKABLE TRIPODAL CAMERA CONTROL UNIT, filed Feb. 22, 2013 and U.S. patent application Ser. No. 13/754,767, entitled ADJUSTABLE VARIABLE RESOLUTION INSPECTION SYSTEMS AND METHODS, filed Jan. 30, 2013, the content of which is incorporated by reference herein.

Some embodiments may include elements such as a lid or other cover element for all or portions of displays or controls of the device. The lid or cover element may include a switch, which may be coupled to a control circuit to control operational parameters of the device, such as full or selective power control of elements of the controller, display turn-off or dimming, and the like. The controller may include a hood, which may be configured with a release mechanism to be removable and/or maintained with a frictional contact. Some embodiments may be configured to couple with a tablet, smartphone, or other device, either via wired or wireless connections, to transfer data, control signals, images, video streams, and the like. Some embodiments may include an internal battery or batteries. The internal battery may be configured to be chargeable by an external battery or other external power source. In this configuration, the internal battery may be used for operation when the external battery is removed or the charge is drained or the battery is otherwise low on power. Example voltages for external and corresponding internal batteries may be approximately 18 volts DC and approximately 15 volts DC, or other voltages in alternate embodiments.

Clearly, other embodiments and modifications of this disclosure may occur readily to those of ordinary skill in the art in view of these teachings. Therefore, the protection afforded this disclosure is to be limited only by the following claims, which include all such embodiments and modifications when viewed in conjunction with the above specification and accompanying drawing.

In some configurations, the apparatus, circuit, modules, or systems described herein may include means for implementing features or providing functions described herein. In one aspect, the aforementioned means may be a module including a processing element with a processor or processors, associated memory and/or other electronics in which embodiments of the disclosure reside, such as to implement signal processing, switching, transmission, reception, or other functions to process video or data signal inputs, control functions, and/or to provide other electronic functions described herein. These may be, for example, modules or apparatus residing in pipe inspection systems, camera controllers, pipe inspection platforms, electronics modules, user interface modules, display devices, electronic computing devices, apparatus for coupling signals to pipes or other buried or hidden objects, and/or other related equipment or devices for pipe and cavity inspection and/or imaging.

In one or more exemplary embodiments, the electronic functions, methods and processes described herein and associated with pipe inspection systems, camera controller units, electronics modules, electronic computing devices, display devices, video systems, coupling apparatus, and other pipe inspection system components such as cable reels and related electronics may be implemented in hardware, software, firmware, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

As used herein, computer program products comprising computer-readable media including all forms of computer-readable medium except, to the extent that such media is deemed to be non-statutory, transitory propagating signals.

It is understood that the specific order or hierarchy of steps or stages in the processes and methods disclosed herein are examples of exemplary approaches. Based upon design preferences, it is understood that the specific order or hierarchy of steps in the processes may be rearranged while remaining within the scope of the present disclosure unless noted otherwise.

Those of skill in the art would understand that information and signals, such as video and/or audio signals or data, control signals, or other signals or data may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, electro-mechanical components, or combinations thereof. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein and, for example, in a processing element as described herein may be implemented or performed with a general purpose processor or processors, a digital signal processor (DSP), an application specific integrated circuit (ASIC), a field programmable gate array (FPGA) or other programmable logic device, discrete gate or transistor logic, discrete hardware components, or any combination thereof designed to perform the processing functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. A processing element may furthering include or be coupled to one or more memory elements for storing instructions, data, and/or other information in a digital storage format.

The various illustrative functions and circuits described in connection with the embodiments disclosed herein with respect to camera controllers, video systems, associated lighting systems, audio and video signal processing, pipe inspection system operational control, and other electronic processing functions described herein may be implemented or performed in processing module or element with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known or developed in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The scope of the present invention is not intended to be limited to the aspects shown herein, but is to be accorded the full scope consistent with the specification and drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure. Thus, the disclosure is not intended to be limited only to the aspects shown herein but is to be accorded the widest scope consistent with the appended claims and their equivalents.

We claim:

1. A camera controller, comprising:
   a base assembly to mechanically couple the camera controller to a hidden or buried pipe inspection system that includes a video push-cable and a camera head coupled to the video push-cable;
   a user interface panel disposed on or within the base assembly;
   an electronics module electrically coupled to the user interface panel including programmable electronic circuitry for:
   receiving control input signals from the user interface panel upon a user actuation and providing, responsive to the received input signals, control data to the pipe inspection system camera head to control video capture operation; and
   receiving one or more pipe inspection output video signals from the pipe inspection system camera head and storing data corresponding to the pipe inspection output video signals in a non-transitory memory;
   a transmitter lug; and
   an internal transmitter for generating a signal at at least a single frequency to be coupled onto the video push-cable via the transmitter lug to generate corresponding magnetic field signals for detection by an associated utility locator.

2. The camera controller of claim 1, wherein the electronics module includes additional electronic circuitry to provide the data corresponding to the pipe inspection output signals to an external electronic computing system.

3. The camera controller of claim 1, wherein the pipe inspection system includes a cable reel drum assembly.

4. The controller of claim 1, further comprising a Universal Serial Bus (USB) hub coupled to the electronics module to send and/or receive data associated with a pipe or other cavity being inspected.

5. The controller of claim 1, further comprising an electrical connector coupled to the electronics module for receiving signals from a system cable connected to the pipe inspection system.

6. The controller of claim 1, further comprising a wireless communication module coupled to the electronics module for sending and/or receiving wireless communication signals.

7. The controller of claim 1, further comprising a hub or router configured to wirelessly send and/or receive information from the pipe inspection system.

8. The controller of claim 7, wherein the information provided from the hub or router includes image, audio, and/or video data.

9. The controller of claim 1, wherein the transmitter generates a signal at a plurality of frequencies to be coupled onto the associated pipe inspection push-cable through the transmitter lug.

10. The controller of claim 1, wherein the camera controller includes one or more of a frame, feet, and a casing, and wherein the frame, the feet, and/or the casing are positioned on the camera controller to provide a grounding connection between the transmitter and a ground surface when the camera controller is placed on the ground surface.

11. The controller of claim 1, further including a microphone, wherein the electronics module receives an audio signal from the microphone, associates the audio signal with the pipe inspection output signals, and stores the audio signal and the pipe inspection output signals in a non-transitory memory.

12. The controller of claim 11, wherein the processing module is programmed to integrate the pipe inspection output signals, positional data provided from a positional sensor, and the audio signal and store the resulting data in the non-transitory memory.

13. The controller of claim 1, wherein the camera head includes a camera and a high-speed data link, wherein the camera is equipped with one or more of orientation, movement, and positional sensors.

14. The controller of claim 13, wherein the camera includes a microphone.

15. The controller of claim 1, comprising one or more stepped USB connectors.

16. The controller of claim 15, further comprising a sealed cover for the one or more stepped USB connectors.

17. The controller of claim 1, further comprising a joystick.

18. The controller of claim 17, wherein the joystick receives one or more of user inputs for traction manipulation, cursor movement, and image manipulation/articulation and provides corresponding outputs to the electronics module.

19. The controller of claim 1, further comprising a magnetically sensed user interface device (UID).

20. The controller of claim 1, further comprising an internal battery; wherein the internal battery is configured to be charged from an external battery or external power supply.

21. The controller of claim 1, further comprising a lid element and a magnetic switch disposed on or within the lid element to control power actuation responsive to the a lid element open or closed position.

22. The controller of claim 1, further comprising a hood element.

23. The controller of claim 22, wherein the hood element is removable.

24. The controller of claim 23, wherein the hood element is restrained using a frictional surface contact.

* * * * *